United States Patent
Niehaus et al.

(10) Patent No.: US 10,918,907 B2
(45) Date of Patent: Feb. 16, 2021

(54) AUTOMATIC DETECTION AND QUANTIFICATION OF SWIMMING

(71) Applicant: Fitbit, Inc., San Francisco, CA (US)

(72) Inventors: Logan Niehaus, Alameda, CA (US); Subramaniam Venkatraman, Walnut Creek, CA (US); Jonathan Wonwook Kim, Emeryville, CA (US)

(73) Assignee: Fitbit, Inc., San Francisco, CA (US)

( * ) Notice: Subject to any disclaimer, the term of this patent is extended or adjusted under 35 U.S.C. 154(b) by 576 days.

(21) Appl. No.: 15/676,831

(22) Filed: Aug. 14, 2017

(65) Prior Publication Data

US 2018/0043210 A1 Feb. 15, 2018

Related U.S. Application Data

(60) Provisional application No. 62/374,901, filed on Aug. 14, 2016, provisional application No. 62/380,339, filed on Aug. 26, 2016.

(51) Int. Cl.
*A63B 24/00* (2006.01)
*G09B 19/00* (2006.01)
(Continued)

(52) U.S. Cl.
CPC ............ *A63B 24/0006* (2013.01); *A61B 5/11* (2013.01); *A61B 5/1118* (2013.01);
(Continued)

(58) Field of Classification Search
None
See application file for complete search history.

(56) References Cited

U.S. PATENT DOCUMENTS

| | | |
|---|---|---|
| 4,367,752 A | 1/1983 | Jimenez et al. |
| 4,526,036 A | 7/1985 | Morrison |

(Continued)

FOREIGN PATENT DOCUMENTS

| | | |
|---|---|---|
| CN | 101330863 | 12/2008 |
| CN | 101518442 | 9/2009 |

(Continued)

OTHER PUBLICATIONS

"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.

(Continued)

*Primary Examiner* — James B Hull
(74) *Attorney, Agent, or Firm* — Weaver Austin Villeneuve & Sampson LLP

(57) ABSTRACT

A wearable device for tracking swim activities of a user is provided. The wearable device may include one or more sensors configured to generate sensor data, and based on the sensor data, the wearable device may determine swim metrics such as swim stroke count, swim stroke type, swim lap count, and swim speed. The determined swim metrics may be filtered based on one or more swim periods during which the user is likely to have been swimming. The wearable device may determine such swim periods based on the sensor data and/or the determined swim metrics.

20 Claims, 15 Drawing Sheets

(51) Int. Cl.
  *G01C 5/06* (2006.01)
  *G01P 15/18* (2013.01)
  *A63B 71/06* (2006.01)
  *G06K 9/00* (2006.01)
  *A61B 5/00* (2006.01)
  *A61B 5/11* (2006.01)
  *A61B 5/145* (2006.01)
  *A61B 5/021* (2006.01)
  *A61B 5/024* (2006.01)
  *A61B 5/0476* (2006.01)
  *A61B 5/0488* (2006.01)

(52) U.S. Cl.
  CPC ............ *A61B 5/4866* (2013.01); *A61B 5/681* (2013.01); *A63B 71/0622* (2013.01); *G01C 5/06* (2013.01); *G01P 15/18* (2013.01); *G06K 9/00342* (2013.01); *G09B 19/0038* (2013.01); *A61B 5/021* (2013.01); *A61B 5/024* (2013.01); *A61B 5/0476* (2013.01); *A61B 5/0488* (2013.01); *A61B 5/14532* (2013.01); *A61B 2562/029* (2013.01); *A61B 2562/0219* (2013.01); *A61B 2562/0271* (2013.01); *A63B 2024/0009* (2013.01); *A63B 2208/03* (2013.01); *A63B 2220/12* (2013.01); *A63B 2220/17* (2013.01); *A63B 2220/30* (2013.01); *A63B 2220/62* (2013.01); *A63B 2220/803* (2013.01); *A63B 2220/836* (2013.01); *A63B 2225/50* (2013.01); *A63B 2244/20* (2013.01); *G09B 19/00* (2013.01)

(56) References Cited

U.S. PATENT DOCUMENTS

| | | |
|---|---|---|
| 4,771,792 A | 9/1988 | Seale |
| 4,780,085 A * | 10/1988 | Malone ................ A63B 71/06 340/323 R |
| 5,036,856 A | 8/1991 | Thornton |
| 5,101,831 A | 4/1992 | Koyama et al. |
| 5,318,597 A | 6/1994 | Hauck et al. |
| 5,612,931 A | 3/1997 | Sato et al. |
| 5,738,104 A | 4/1998 | Lo et al. |
| 6,131,076 A | 10/2000 | Stephan et al. |
| 6,241,684 B1 | 6/2001 | Amano et al. |
| 6,418,394 B1 | 7/2002 | Puolakanaho et al. |
| 6,418,797 B1 | 7/2002 | Ambrosina et al. |
| 6,583,369 B2 | 6/2003 | Montagnino et al. |
| 6,720,860 B1 | 4/2004 | Narayanaswami |
| 6,731,967 B1 | 5/2004 | Turcott |
| 7,539,532 B2 | 5/2009 | Tran |
| 7,815,549 B2 | 10/2010 | Crawford et al. |
| 8,152,745 B2 | 4/2012 | Smith et al. |
| 8,211,503 B2 | 7/2012 | Tsao et al. |
| 8,346,328 B2 | 1/2013 | Mannheimer et al. |
| 8,386,042 B2 | 2/2013 | Yudovsky et al. |
| 8,444,578 B2 | 5/2013 | Bourget et al. |
| 8,475,367 B1 | 7/2013 | Yuen et al. |
| 8,579,827 B1 | 11/2013 | Rulkov et al. |
| 8,762,101 B2 | 6/2014 | Yuen et al. |
| 8,792,981 B2 | 7/2014 | Yudovsky et al. |
| 8,849,610 B2 | 9/2014 | Molettiere et al. |
| 8,920,332 B2 | 12/2014 | Hong et al. |
| 8,945,017 B2 | 2/2015 | Venkatraman et al. |
| 8,948,832 B2 | 2/2015 | Hong et al. |
| 8,956,303 B2 | 2/2015 | Hong et al. |
| 8,998,815 B2 | 4/2015 | Venkatraman et al. |
| 9,005,129 B2 | 4/2015 | Venkatraman et al. |
| 9,042,971 B2 | 5/2015 | Brumback et al. |
| 9,044,149 B2 | 6/2015 | Richards et al. |
| 9,044,150 B2 | 6/2015 | Brumback et al. |
| 9,049,998 B2 | 6/2015 | Brumback et al. |
| 9,079,060 B2 | 7/2015 | Hong et al. |
| 9,113,794 B2 | 8/2015 | Hong et al. |
| 9,113,795 B2 | 8/2015 | Hong et al. |
| 9,168,419 B2 | 10/2015 | Hong et al. |
| 9,202,111 B2 | 12/2015 | Arnold et al. |
| 9,237,855 B2 | 1/2016 | Hong et al. |
| 9,410,979 B2 | 8/2016 | Yuen et al. |
| 9,456,787 B2 | 10/2016 | Venkatraman et al. |
| 9,504,408 B2 | 11/2016 | Hong et al. |
| 9,596,990 B2 | 3/2017 | Park et al. |
| 9,603,524 B2 | 3/2017 | Park et al. |
| 9,655,548 B2 | 5/2017 | Hong et al. |
| 9,712,629 B2 | 7/2017 | Molettiere et al. |
| 9,750,977 B2 | 9/2017 | Yuen et al. |
| 10,327,674 B2 | 6/2019 | Hong et al. |
| 2001/0044588 A1 | 11/2001 | Mault |
| 2003/0208133 A1 | 11/2003 | Mault |
| 2004/0236227 A1 | 11/2004 | Gueissaz |
| 2005/0054940 A1 | 3/2005 | Almen |
| 2005/0103129 A1 | 5/2005 | Karason |
| 2005/0177059 A1 | 8/2005 | Koivumaa et al. |
| 2005/0245793 A1 | 11/2005 | Hilton et al. |
| 2008/0097221 A1 | 4/2008 | Florian |
| 2008/0190202 A1 | 8/2008 | Kulach et al. |
| 2008/0249836 A1 | 10/2008 | Angell et al. |
| 2009/0012433 A1 | 1/2009 | Fernstrom et al. |
| 2010/0106044 A1 | 4/2010 | Linderman |
| 2010/0152600 A1 | 6/2010 | Droitcour et al. |
| 2010/0204952 A1 | 8/2010 | Irlam et al. |
| 2010/0249633 A1 | 9/2010 | Droitcour et al. |
| 2010/0263468 A1 | 10/2010 | Fisher et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0331145 A1 | 12/2010 | Lakovic et al. |
| 2010/0331657 A1 | 12/2010 | Mensinger et al. |
| 2011/0003665 A1 * | 1/2011 | Burton ................ G04G 9/007 482/9 |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2012/0019381 A1 | 1/2012 | Yuen |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0255875 A1 | 10/2012 | Vicente et al. |
| 2012/0274508 A1 | 11/2012 | Brown et al. |
| 2012/0316471 A1 | 12/2012 | Rahman et al. |
| 2012/0330572 A1 | 12/2012 | Longman |
| 2013/0009013 A1 | 1/2013 | Bourakov et al. |
| 2013/0009779 A1 | 1/2013 | Wittling et al. |
| 2013/0073254 A1 | 3/2013 | Yuen et al. |
| 2013/0073255 A1 | 3/2013 | Yuen et al. |
| 2013/0077826 A1 | 3/2013 | Cowperthwaite et al. |
| 2013/0080113 A1 | 3/2013 | Yuen et al. |
| 2013/0104650 A1 | 5/2013 | Bailey et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0163390 A1 | 6/2013 | Gossweiler, III et al. |
| 2013/0194066 A1 | 8/2013 | Rahman et al. |
| 2013/0205896 A1 | 8/2013 | Baechler |
| 2013/0234924 A1 | 9/2013 | Janefalkar et al. |
| 2013/0254525 A1 | 9/2013 | Johnson et al. |
| 2013/0280682 A1 | 10/2013 | Levine et al. |
| 2013/0332156 A1 | 12/2013 | Tackin et al. |
| 2014/0073486 A1 | 3/2014 | Ahmed et al. |
| 2014/0099614 A1 | 4/2014 | Hu et al. |
| 2014/0149066 A1 | 5/2014 | Holopainen |

(56) References Cited

U.S. PATENT DOCUMENTS

| | | | |
|---|---|---|---|
| 2014/0156043 A1 | 6/2014 | Blackadar et al. | |
| 2014/0275821 A1 | 9/2014 | Beckman | |
| 2014/0275854 A1 | 9/2014 | Venkatraman et al. | |
| 2014/0278139 A1 | 9/2014 | Hong et al. | |
| 2014/0278229 A1 | 9/2014 | Hong et al. | |
| 2014/0303523 A1 | 10/2014 | Hong et al. | |
| 2014/0358473 A1 | 12/2014 | Goel et al. | |
| 2014/0378786 A1 | 12/2014 | Hong et al. | |
| 2014/0378872 A1 | 12/2014 | Hong et al. | |
| 2015/0057945 A1* | 2/2015 | White | A61B 5/0022 702/19 |
| 2015/0097700 A1 | 4/2015 | Holthouse | |
| 2015/0100245 A1 | 4/2015 | Huang et al. | |
| 2016/0051169 A1 | 2/2016 | Hong et al. | |
| 2016/0084869 A1 | 3/2016 | Yuen et al. | |
| 2016/0128625 A1 | 5/2016 | Lee et al. | |
| 2018/0042526 A1 | 2/2018 | Hong et al. | |
| 2018/0055376 A1 | 3/2018 | Yuen et al. | |
| 2018/0160943 A1 | 6/2018 | Fyfe et al. | |

FOREIGN PATENT DOCUMENTS

| | | |
|---|---|---|
| CN | 102481479 | 5/2012 |
| CN | 102835951 | 12/2012 |
| CN | 102858236 | 1/2013 |
| EP | 1 721 237 | 8/2012 |
| WO | WO 07/102134 | 9/2007 |

OTHER PUBLICATIONS

"Golf Club Sensor System: Game Golf" Postscapes Tracking the Internet of Things. Downloaded Apr. 2, 2014. 3 pp.

"Meet GolfSense," Zepp GolfSense | The #1 Golf Swing Analyzer for iPhone, iPad, Android, Zepp,Downloaded from the internet at http://www.zepp.com/golf/sense/ on Apr. 2, 2014, 10 pp.

"Parts of Your Band," (Product Release Date Unknown, downloaded Jul. 22, 2013) Jawbone UP Band, 1 page.

Withings pulse, Quick Installation Guide (Jul. 24, 2013) Withings Pulse QIG, v 1.3, withings.com/pulse, 16 pp.

Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.

Connaghan et al., 2011, Multi-Sensor Classification of Tennis Strokes, 4 pp.

Cooper, Aug. 16, 2013, Withings Pulse review, http://www.engadget.com/2013/08/16/withings-pulse-revew/, 8 pp.

Delporte et al., Mar. 2012, Accelerometer and Magnetometer Based Gyroscope Emulation on Smart Sensor for a Virtual Reality Application, Sensors & Transducers.

DesMarais, Christina (posted on Sep. 3, 2013) "Which New Activity Tracker is Best for You?" Health and Home, Health & Fitness, Guides & Reviews, [Retrieved on Sep. 23, 2013 at http://www.techlicious.com/guide/which-new-activity-tracker-is-right-for-- you/] 4 pp.

Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.

Fitbit User's Manual, Last Updated Oct. 22, 2009, 15 pp.

Forerunner® 10 Owner's Manual (Aug. 2012), Garmin Ltd., 10 pp.

Forerunner® 110 Owner's Manual, (2010) "GPS-Enabled Sport Watch," Garmin Ltd., 16 pp.

Forerunner® 201 personal trainer owner's manual, (Feb. 2006) Garmin Ltd., 48 pp.

Forerunner® 205/305 Owner's Manual, GPS-enabled trainer for runners, (2006-2008), Garmin Ltd., 80 pp.

Forerunner® 210 Owner's Manual, (2010) "GPS-Enabled Sport Watch," Garmin Ltd., 28 pp.

Forerunner® 301 personal trainer owner's manual, (Feb. 2006) Garmin Ltd., 66 pp.

Forerunner® 310XT Owner's Manual, Multisport GPS Training Device, (2009-2013), Garmin Ltd., 56 pp.

Forerunner® 405 Owner's Manual, (Mar. 2011) "GPS-Enabled Sport Watch With Wireless Sync," Garmin Ltd., 56 pp.

Forerunner® 405CX Owner's Manual, "GPS-Enabled Sports Watch With Wireless Sync," (Mar. 2009), Garmin Ltd., 56 pp.

Forerunner® 410 Owner's Manual, (Jul. 2012) "GPS-Enabled Sport Watch With Wireless Sync," Garmin Ltd., 52 pp.

Forerunner® 50 with ANT+Sport™ wireless technology, Owner's Manual, (Nov. 2007) Garmin Ltd., 44 pp.

Forerunner® 910XT Owner's Manual, (Jan. 2013) Garmin Ltd., 56 pp.

Garmin Swim™ Owner's Manual (Jun. 2012), 10 pp.

Golf Club Sensor System: Game Golf, Postscapes™ Tracking the Internet of Things, Downloaded at http://postscapes.com/golf-club-sensor-system-game-golf, on Apr. 2, 2014, 3 pp.

Nguyen et al., Apr. 2011, A Wearable Sensing System for Tracking and Monitoring of Functional Arm Movement, IEEE/ASME Transactions on Mechatronics, 16(2):213-220.

Nike+ FuelBand GPS Manual, User's Guide (Product Release Date Unknown, downloaded Jul. 22, 2013), 26 pp.

Nike+SportWatch GPS Manual, User's Guide, Powered by TOMTOM, (Product Release Date Unknown, downloaded Jul. 22, 2013), 42 pp.

Polar WearLink@+ Coded Transmitter 31 Coded Transmitter W.I.N.D. User Manual, POLAR@ Listen to Your Body, Manufactured by Polar Electro Oy, 11 pp.

Rainmaker, (Jul. 25, 2013) "Basis B1 Watch In-Depth Review," [retrieved on Feb. 4, 2014 at http://www.dcrainmaker.com/2013/07/basis-b1-review.html], 56 pp.

Rose, Brent "Garmin's Edge 1000 May Be the Smartest Bike Computer Yet" Gizmodo, Downloaded at http://gizmodo.com/garmins-edge-1000-may-be-the-smartest-bike-computer-ye- -1561155835 on Apr. 9, 2014. 4 pp.

Stanley, Michael E. (Mar. 12, 2013) "Building a virtual gyro," The Embedded Beat, Freescale, Inc. downloaded from the internet at https://community.freescale.com/community/the-embedded-beat/blog/2013/03/- 12/building- . . . on Apr. 2, 2014, 6 pp.

Zhan et al. (Nov. 6-9, 2012) "Accurate Caloric Expenditure of Bicyclists Using Cellphones," SenSys '12, 14 pp.

Zijlstra, Wiebren, (2004) "Assessment of spatio-temporal parameters during unconstrained walking," Eur J Appl Physiol, 92:39-44.

U.S. Office Action, dated Mar. 2, 2015, issued in U.S. Appl. No. 14/292,741.

U.S. Final Office Action, dated Jun. 15, 2015, issued in U.S. Appl. No. 14/292,741.

U.S. Notice of Allowance, dated Aug. 11, 2015, issued in U.S. Appl. No. 14/292,741.

U.S. Office Action, dated Jun. 2, 2016, issued in U.S. Appl. No. 14/921,626.

U.S. Final Office Action, dated Sep. 30, 2016, issued in U.S. Appl. No. 14/921,626.

U.S. Notice of Allowance, dated Jan. 11, 2017, issued in U.S. Appl. No. 14/921,626.

U.S. Notice of Allowance, dated Apr. 19, 2017, issued in U.S. Appl. No. 14/921,626.

U.S. Office Action, dated May 30, 2018, issued in U.S. Appl. No. 15/601,599.

U.S. Final Office Action, dated Oct. 9, 2018, issued in U.S. Appl. No. 15/601,599.

U.S. Notice of Allowance, dated Feb. 8, 2019, issued in U.S. Appl. No. 15/601,599.

Chinese First Office Action, dated Jul. 5, 2016, issued in Application No. CN 201410243248.0 [FTBTP002X1ICN].

Chinese Second Office Action, dated Feb. 3, 2017, issued in Application No. CN 201410243248.0.

Chinese Third Office Action, dated Jun. 13, 2017, issued in Application No. CN 201410243248.0.

Chinese Fourth Office Action, dated Sep. 25, 2017, issued in Application No. CN 201410243248.0.

Garmin Swim™ Owner's Manual (Jun. 2012), 12 pp.

(56) References Cited

OTHER PUBLICATIONS

Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
"Using MS5534 for altimeters and barometers," *Intersema AN501, Application Note*, Jan. 2006, 12 pp.
Yang, Che-Chang, "A Review of Accelerometry-BaSED Wearable Motion Detectors for Physical Activity Monitoring," published Aug. 20, 2010, Sensors 2010. 17 pp.
U.S. Office Action, dated Jan. 13, 2020, issued in U.S. Appl. No. 15/720,634.
U.S. Final Office Action, dated Apr. 23, 2020, issued in U.S. Appl. No. 15/720,634.
U.S. Notice of Allowance, dated Aug. 7, 2020, issued in U.S. Appl. No. 15/720,634.
Chinese First Office Action, dated Mar. 29, 2017, issued in Application No. CN 201610384077.2.
Chinese Second Office Action, dated Dec. 8, 2017, issued in Application No. CN 201610384077.2.
Nguyen, Kim Doang, "A Body Sensor Network for Tracking and Monitoring of Functional Arm Motion," published on Oct. 11-15, 2009. St. Louis, USA, 6 pages.
Retscher (2006) "An Intelligent Multi-sensor System for Pedestrian Navigation," *Journal of Global Positioning Systems*, 5(1):110-118.

* cited by examiner

AUTOMATIC DETECTION AND QUANTIFICATION OF SWIMMING

RELATED APPLICATIONS

This application claims the benefit of U.S. Provisional Patent Application No. 62/374,901, filed Aug. 14, 2016 and titled "AUTOMATIC DETECTION AND QUANTIFICATION OF SWIMMING" and U.S. Provisional Patent Application No. 62/380,339, filed Aug. 26, 2016 and titled "AUTOMATIC DETECTION AND QUANTIFICATION OF SWIMMING," the disclosures of which are hereby incorporated by reference in their entirety.

TECHNICAL FIELD

This disclosure relates to the field of wearable devices, and particularly to automatic detection and quantification of user activities such as swimming.

BACKGROUND

Consumer interest in personal health has led to a variety of personal health monitoring devices being offered on the market. Such devices, until recently, tended to be complicated to use and were typically designed for use with one activity, for example, bicycle trip computers.

Advances in sensors, electronics, and power source miniaturization have allowed the size of personal health monitoring devices, also referred to herein as "biometric tracking," "biometric monitoring," or simply "wearable" devices, to be offered in extremely small sizes that were previously impractical. The number of applications for these devices is increasing as the processing power and component miniaturization for wearable devices improves.

SUMMARY

The systems, methods and devices of this disclosure each have several innovative aspects, no single one of which is solely responsible for the desirable attributes disclosed herein.

In one aspect, there is provided a method of operating a wearable device, the wearable device comprising one or more sensors. The method may involve: receiving sensor data generated by the one or more sensors; generating activity metrics specific to a user activity based on the sensor data (e.g., without determining that a user of the wearable device is performing the user activity or receiving an indication that the user is performing the user activity), the activity metrics indicative of the user's performance with respect to the user activity; determining one or more activity periods during which the user is likely to have been performing the user activity based on the sensor data; filtering the activity metrics based on the one or more determined activity periods such that a portion of the activity metrics that does not temporally overlap with the one or more activity periods is removed; and outputting the filtered activity metrics for presentation to the user. The method may further involve: generating the activity metrics over a first time period, the generated activity metrics comprising a series of values each corresponding to a unit time period within the first time period; and determining, at a second time period subsequent to the first time period, the one or more activity periods within the first time period. The method may further involve identifying a first activity period starting at a first point in time within the first time period and ending at a second point in time within the first time period based on a determination that the sensor data generated during the first time period indicates that the user started performing the user activity at the first point in time and continued to perform the user activity until the second point in time.

In another aspect, there is provided a wearable device, including one or more sensors and at least one processor configured to receive sensor data generated by the one or more sensors. The wearable device may further include a memory storing computer-executable instructions for controlling the at least one processor to: receive sensor data generated by the one or more sensors; generate activity metrics specific to the user activity based on the sensor data (e.g., without determining that a user of the wearable device is performing the user activity or receiving an indication that the user is performing the user activity), the activity metrics indicative of the user's performance with respect to the user activity; determine one or more activity periods during which the user is likely to have been performing the user activity based on the sensor data; filter the activity metrics based on the one or more determined activity periods such that a portion of the activity metrics that does not temporally overlap with the one or more activity periods is removed; and output the filtered activity metrics for presentation to the user. The at least one processor may further be controlled to: generate the activity metrics over a first time period, the generated activity metrics comprising a series of values each corresponding to a unit time period within the first time period; and determine, at a second time period subsequent to the first time period, the one or more activity periods within the first time period. The at least one processor may further be controlled to identify a first activity period starting at a first point in time within the first time period and ending at a second point in time within the first time period based on a determination that the sensor data generated during the first time period indicates that the user started performing the user activity at the first point in time and continued to perform the user activity until the second point in time.

In yet another aspect, there is provided non-transitory physical computer storage having stored thereon instructions that, when executed, cause one or more processors of a wearable device to: receive sensor data generated by the one or more sensors; generate activity metrics specific to the user activity based on the sensor data (e.g., without determining that a user of the wearable device is performing the user activity or receiving an indication that the user is performing the user activity), the activity metrics indicative of the user's performance with respect to the user activity; determine one or more activity periods during which the user is likely to have been performing the user activity based on the sensor data; filter the activity metrics based on the one or more determined activity periods such that a portion of the activity metrics that does not temporally overlap with the one or more activity periods is removed; and output the filtered activity metrics for presentation to the user. The instructions may further cause the one or more processors to: generate the activity metrics over a first time period, the generated activity metrics comprising a series of values each corresponding to a unit time period within the first time period; and determine, at a second time period subsequent to the first time period, the one or more activity periods within the first time period. The instructions may further cause the one or more processors to identify a first activity period starting at a first point in time within the first time period and ending at a second point in time within the first time period based on a determination that the sensor data generated during the first time period indicates that the user started performing the user activity at the first point in time and continued to perform the user activity until the second point in time.

In yet another aspect, there is provided a method of operating a wearable device, the wearable device comprising one or more sensors. The method may involve: receiving sensor data generated by the one or more sensors; based on the sensor data generated during a first time period, determining whether a user of the wearable device is performing a user activity (e.g., without receiving an input from the user indicative of whether the user is performing the user activity); and in response to a determination that the user is performing the user activity, performing one or more of (i) generating one or more activity metrics specific to the user activity (e.g., based on the sensor data generated during the first time period, based on sensor data generated during a second time period that is subsequent to the first time period, or based on sensor data generated during the first and second time periods), (ii) activating one or more additional sensors for generating additional sensor data related to the user activity, and (iii) activating an activity mode corresponding to the user activity to monitor the user's progress and/or performance with respect to the user activity.

In yet another aspect, there is provided a wearable device, including one or more sensors and at least one processor configured to receive sensor data generated by the one or more sensors. The wearable device may further include a memory storing computer-executable instructions for controlling the at least one processor to: based on sensor data generated by one or more sensors during a first time period, determine whether a user of the wearable device is performing a user activity (e.g., without receiving an input from the user indicative of whether the user is performing the user activity); and in response to a determination that the user is performing the user activity, perform one or more of (i) generate one or more activity metrics specific to the user activity (e.g., based on the sensor data generated during the first time period, based on sensor data generated during a second time period that is subsequent to the first time period, or based on sensor data generated during the first and second time periods), (ii) activate one or more additional sensors for generating additional sensor data related to the user activity, and (iii) activate an activity mode corresponding to the user activity, the activity mode configured to monitor the user's progress and/or performance with respect to the user activity.

In yet another aspect, there is provided non-transitory physical computer storage having stored thereon instructions that, when executed, cause one or more processors of a wearable device to: based on sensor data generated by one or more sensors during a first time period, determine whether a user of the wearable device is performing a user activity (e.g., without receiving an input from the user indicative of whether the user is performing the user activity); and in response to a determination that the user is performing the user activity, perform one or more of (i) generate one or more activity metrics specific to the user activity (e.g., based on the sensor data generated during the first time period, based on sensor data generated during a second time period that is subsequent to the first time period, or based on sensor data generated during the first and second time periods), (ii) activate one or more additional sensors for generating additional sensor data related to the user activity, and (iii) activate an activity mode corresponding to the user activity, the activity mode configured to monitor the user's progress and/or performance with respect to the user activity.

In yet another aspect, there is provided a method of detecting swimming activity of a user of a wearable device, the wearable device comprising one or more sensors. The method may involve: obtaining sensor data generated by the one or more sensors; determining, based on the sensor data, swim metrics indicative of the user's performance with respect to swimming; identifying, based on the sensor data, one or more swim periods during which the user may have been swimming; filtering the swim metrics based on the one or more identified swim periods to remove at least one portion of the swim metrics that does not temporally overlap with the one or more swim periods; and outputting the filtered swim metrics for presentation to the user.

The method of the preceding paragraph can have any sub-combination of the following features: where the method further involves determining the swim metrics over a first time period, the determined swim metrics comprising a series of values each corresponding to a unit time period within the first time period, and determining, at a second time period subsequent to the first time period, the one or more swim periods within the first time period; where the method further involves identifying a first swim period starting at a first point in time within the first time period and ending at a second point in time within the first time period based on a determination that the sensor data generated during the first time period is indicative of the user having (i) started swimming at the first point in time, (ii) continued to swim until the second point in time, and (iii) stopped swimming at the second point in time; where the method further involves identifying a first swim period starting at a first point in time within the first time period and ending at a second point in time within the first time period based on a determination that the sensor data generated during the first time period is indicative of the user having (i) started swimming at the first point in time and (ii) stopped swimming at the second point in time; where the method further involves for each unit time period within a time period for which the swim metrics are determined, determining whether swimming is more likely to have been performed during the unit time period than any other one of a plurality of user activities tracked by the wearable device, and determining the one or more swim periods based on individual unit time periods for which swimming is determined to be more likely to have been performed than any other one of the plurality of user activities tracked by the wearable device; where the method further involves determining the swim metrics without a determination that the user is or may be swimming or an indication that the user is or may be swimming; where the method further involves determining the swim metrics in response to a determination that the user is or may be swimming or in response to an indication that the user is or may be swimming; where the method further involves determining the swim metrics for one or more time periods during which the sensor data is indicative of movement greater than a threshold level; where the method further involves while the swim metrics are being determined, determining whether the sensor data is no longer indicative of movement greater than the threshold level, and in response to determining that the sensor data is no longer indicative of movement greater than the threshold level, ceasing the determination of the swim metrics; where the method further involves determining the swim metrics for one or more time periods during which the sensor data is indicative of the wearable device being worn; where the sensor data indicative of the wearable device being worn indicates movement greater than a threshold level; where the method further involves while the swim metrics are being determined, determining whether the sensor data is no longer indicative of the wearable device being worn, and in response to determining that the sensor data is no longer indicative of the wearable device being worn, ceasing the determination of the swim metrics; where the method further involves determining the swim metrics for one or more time periods during which the sensor data is indicative of the user swimming; where the sensor data comprises altimeter data indicative of a pressure change, the method further involving determining that the sensor data is indicative of the user swimming based on the altimeter data; where the sensor data comprises user motion data, the method further involving determining that the sensor data is indicative of the user swimming based on a determination that the user motion data matches a set of predefined motion data associated with swimming; where the method further involves determining the swim metrics as long as the sensor data is being generated by the one or more sensors; where the swim metrics comprise one or more of swim stroke count, swim stroke type, swim kick count, swim lap count, swim lap duration, swim lap start time, swim lap end time, and swim speed; where the method further involves counting swim strokes performed by the user based on a number of acceleration peaks extracted from the sensor data that satisfy a set of predefined rules associated with a swim stroke; where the method further involves counting swim laps performed by the user based on a number of breaks between acceleration peaks extracted from the sensor data that span a threshold time period; where the method further involves counting swim laps performed by the user based on a number of acceleration peaks extracted from the sensor data that satisfy a set of predefined rules associated with a flip turn; where wherein the one or more sensors include an inertial measurement unit, the method further involving counting swim strokes performed by the user based on one or more features extracted from the sensor data generated by the inertial measurement unit; where the one or more sensors include an inertial measurement unit, the method further involving counting swim laps performed by the user based on one or more features extracted from the sensor data generated by the inertial measurement unit; where the wearable device further comprises a geolocation sensor configured to generate geolocation data indicative of a geographic location associated with the swim metrics, the method further involving determining additional swim metrics based on the geographic location associated with the swim metrics; where the method further involves identifying the one or more swim periods during which the user may have been swimming based on a combination of the sensor data and the swim metrics; where the method further involves displaying the filtered swim metrics on a display screen of the wearable device; where the method further involves displaying the filtered swim metrics on a display screen associated with a client device configured to communicate wirelessly with the wearable device; where the method is performed by the wearable device; where the method is performed by a client device configured to communicate wirelessly with the wearable device; and where the wearable device further comprises a memory, the method further involving storing the determined swim metrics in the memory as the swim metrics are determined.

In yet another aspect, there is provided a method of detecting swimming activity of a user of a wearable device, the wearable device comprising one or more sensors. The method may involve: obtaining sensor data generated by the one or more sensors from the wearable device; obtaining swim metrics indicative of the user's performance with respect to swimming from the wearable device; identifying, based on the sensor data, one or more swim periods during which the user may have been swimming; filtering the swim metrics based on the one or more identified swim periods to remove at least one portion of the swim metrics that does not temporally overlap with the one or more swim periods; and outputting the filtered swim metrics for presentation to the user.

The method of the preceding paragraph can have any sub-combination of the following features: where the method is performed by a client device configured to communicate with the wearable device, the method further involving displaying the filtered swim metrics on a display screen of the client device; where the swim metrics are determined over a first time period, the determined swim metrics comprising a series of values each corresponding to a unit time period within the first time period, the method further involving determining, at a second time period subsequent to the first time period, the one or more swim periods within the first time period; where the method further involves identifying a first swim period starting at a first point in time within the first time period and ending at a second point in time within the first time period based on a determination that the sensor data generated during the first time period is indicative of the user having (i) started swimming at the first point in time, (ii) continued to swim until the second point in time, and (iii) stopped swimming at the second point in time; where the method further involves identifying a first swim period starting at a first point in time within the first time period and ending at a second point in time within the first time period based on a determination that the sensor data generated during the first time period is indicative of the user having (i) started swimming at the first point in time and (ii) stopped swimming at the second point in time; where the method further involves for each unit time period within a time period for which the swim metrics are determined, determining whether swimming is more likely to have been performed during the unit time period than any other one of a plurality of user activities tracked by the wearable device, and determining the one or more swim periods based on individual unit time periods for which swimming is determined to be more likely to have been performed than any other one of the plurality of user activities tracked by the wearable device; where the swim metrics are determined without a determination that the user is or may be swimming or an indication that the user is or may be swimming; where the swim metrics are determined in response to a determination that the user is or may be swimming or in response to an indication that the user is or may be swimming; where the swim metrics are determine for one or more time periods during which the sensor data is indicative of movement greater than a threshold level; where the method further involves while the swim metrics are being determined, determining whether the sensor data is no longer indicative of movement greater than the threshold level, and in response to determining that the sensor data is no longer indicative of movement greater than the threshold level, ceasing the determination of the swim metrics; where the swim metrics are determine for one or more time periods during which the sensor data is indicative of the wearable device being worn; where the sensor data indicative of the wearable device being worn indicates movement greater than a threshold level; where the method further involves while the swim metrics are being determined, determining whether the sensor data is no longer indicative of the wearable device being worn, and in response to determining that the sensor data is no longer indicative of the wearable device being worn, ceasing the determination of the swim metrics; wherein the swim metrics are determined for one or more time periods during which the sensor data is indicative of the user swimming; where the sensor data comprises altimeter data indicative of a pressure change, and the swim metrics are determined for the one or more time periods for which the altimeter data is indicative of the user swimming; where the sensor data comprises user motion data, and the swim metrics are determined for the one or more time periods for which the user motion data matches a set of predefined motion data associated with swimming; where the swim metrics comprise one or more of swim stroke count, swim stroke type, swim kick count, swim lap count, swim lap duration, swim lap start time, swim lap end time, and swim speed; where the sensor data further comprises geolocation data indicative of a geographic location associated with the swim metrics, the method further involving determining additional swim metrics based on the geographic location associated with the swim metrics; where the method further involves identifying the one or more swim periods during which the user may have been swimming based on a combination of the sensor data and the swim metrics; where the method further involves periodically obtaining the sensor data and the swim metrics from the wearable device; and where the method further involves obtaining the sensor data and the swim metrics from the wearable device upon establishing of a wireless connection with the wearable device.

In yet another aspect, there is provided a method of detecting swimming activity of a user of a wearable device, the wearable device comprising one or more sensors. The method may involve: receiving sensor data generated by the one or more sensors; determining, based on the sensor data, that the user may be swimming; and determining, based on the sensor data, swim metrics indicative of the user's performance in response to determining that the user may be swimming.

The method of the preceding paragraph can have any sub-combination of the following features: where the method further involves activating one or more additional sensors for generating additional sensor data in response to determining that the user may be swimming; where the method further involves activating a swim mode to monitor the user's progress or performance with respect to swimming in response to determining that the user may be swimming; where the method further involves while determining the swim metrics, determining, based on the sensor data, that the user may no longer be swimming, and in response to determining that the user may no longer be swimming, ceasing the determination of the swim metrics; where the method further involves determining whether the user may be swimming without receiving an input from the user indicative of whether the user is swimming; where the method further involves determining whether the user may be swimming based on a user input indicative of whether the user is swimming; where the method further involves determining whether the user may be swimming based on sensor data generated during a first time period, and generating the swim metrics based on sensor data generated during a second time period that is subsequent to the first time period; where the method further involves determining whether the user may be swimming based on sensor data generated during a first time period, and generating the swim metrics based on a combination of the sensor data generated during the first time period and sensor data generated during a second time period that is subsequent to the first time period; where the method further involves for each unit time period within a time period for which the sensor data is generated, determining whether the user is more likely to be swimming during the unit time period than performing any other one of a plurality of user activities tracked by the wearable device, and generating the swim metrics during one or more individual unit time periods for which the user is determined to be more likely to be swimming than performing any other one of the plurality of user activities tracked by the wearable device; where the swim metrics comprise one or more of swim stroke count, swim stroke type, swim kick count, swim lap count, swim lap duration, swim lap start time, swim lap end time, and swim speed; where the method further involves counting swim strokes performed by the user based on a number of acceleration peaks extracted from the sensor data that satisfy a set of predefined rules associated with a swim stroke; where the method further involves counting swim laps performed by the user based on a number of breaks between acceleration peaks extracted from the sensor data that span a threshold time period; where the method further involves counting swim laps performed by the user based on a number of acceleration peaks extracted from the sensor data that satisfy a set of predefined rules associated with a flip turn; where the one or more sensors include an inertial measurement unit, the method further involving counting swim strokes performed by the user based on one or more features extracted from the sensor data generated by the inertial measurement unit; where the one or more sensors include an inertial measurement unit, the method further involving counting swim laps performed by the user based on one or more features extracted from the sensor data generated by the inertial measurement unit; where the wearable device further comprises a geolocation sensor configured to generate geolocation data indicative of a geographic location associated with the swim metrics, the method further involving determining additional swim metrics based on the geographic location associated with the swim metrics; where the method is performed by the wearable device, the method further involving displaying, on a display screen of the wearable device, a message that comprises at least one of text and graphics indicative of the user's performance with respect to swimming; where the method is performed by a client device that is wirelessly paired with the wearable device, the method further involving transmitting instructions to wearable device to display a message that comprises at least one of text and graphics indicative of the user's performance with respect to swimming; and where the method is performed by a client device that is wirelessly paired with the wearable device, the method further involving displaying, on a display screen associated with the client device, a message that comprises at least one of text and graphics indicative of the user's performance with respect to swimming.

DETAILED DESCRIPTION

Figure 1A:
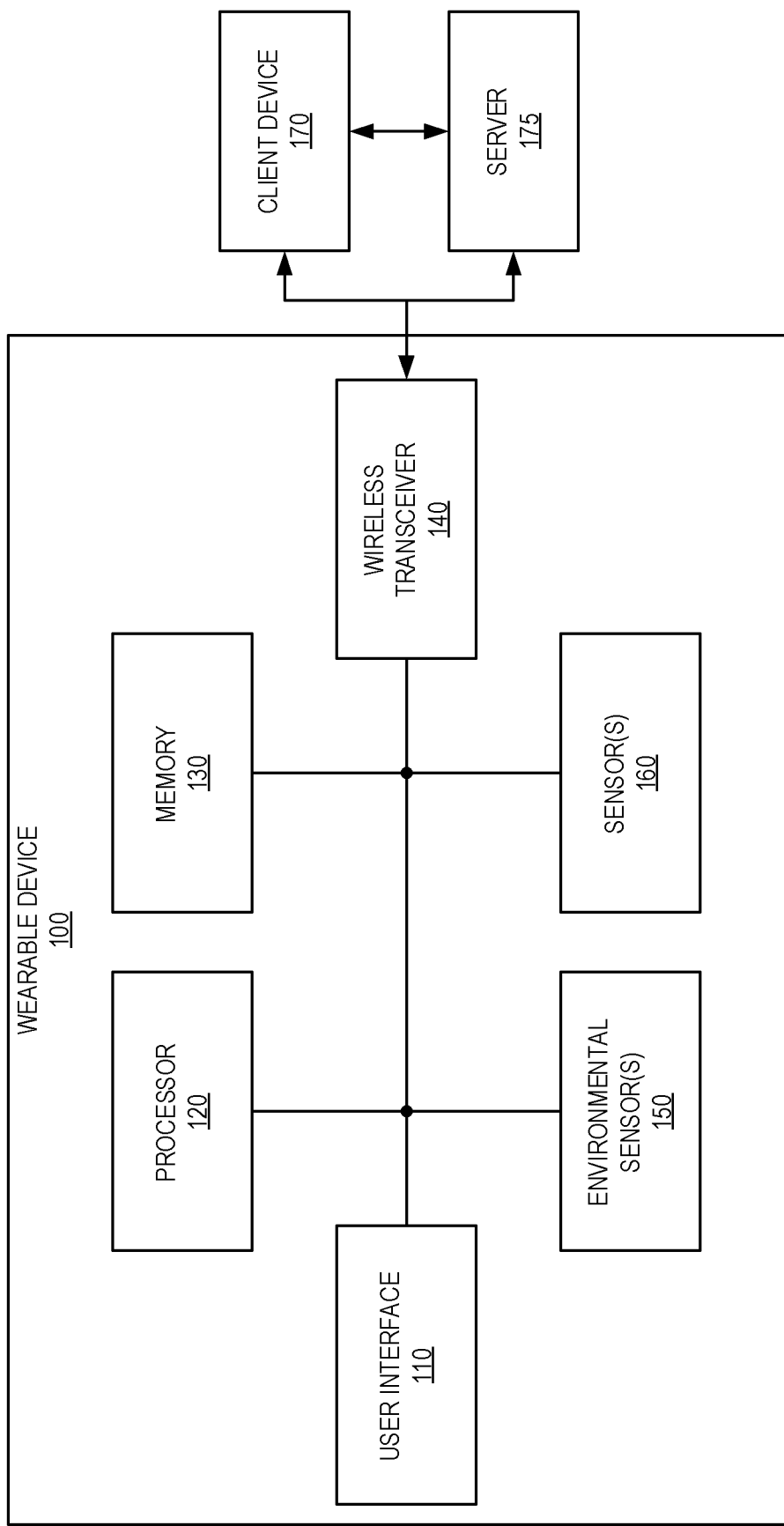
FIG. 1A is a block diagram illustrating certain components of an example wearable device in accordance with aspects of this disclosure.

One of the applications of wearable devices may be the tracking of an exercise performed by a user of a wearable device via one or more sensors. Such wearable devices are sometimes referred to as activity trackers or activity tracking devices. Various algorithms or techniques for tracking exercises have been developed and these algorithms may be specialized based on the type of exercise performed by the user. For example, when the exercise that a user desires to track is swimming, a specialized algorithm for detecting and analyzing the user's swimming may be executed based on data received from one or more sensors such as an accelerometer, a gyroscope, an altimeter, a heart rate monitor, a blood pressure monitor, a global positioning system (GPS) receiver, a gyroscope, a magnetometer, and/or other suitable sensor(s). In addition to swimming, there may be different algorithms for tracking various exercises may include, but are not limited to, outdoor running, indoor/treadmill running, outdoor biking, indoor/stationary biking, hiking, etc. Although the techniques of this disclosure may be described in connection with detecting and tracking swimming activities, this disclosure is not limited to swimming, and may be applicable to other activities.

Automatic Activity Detection

It may be desirable for a wearable device to automatically track an exercise. For example, a user may forget to input the start of an exercise to the wearable device and/or may not wish to take the time to input the start of the exercise. Accordingly, the wearable device may be able to automatically detect that the user has started an exercise based on the output from one or more sensors (e.g., accelerometer, gyroscope, altimeter, heart rate monitor, GPS receiver, etc.) of the wearable device. For example, based on the output of one or more of these sensors, a wearable device may determine that a user has started an exercise and identify the type of exercise that the user has started based on comparing the output of the sensors to defined sensor data for one or more exercise types. Upon identifying the type of exercise that the user has started, the wearable device may provide additional information (e.g., activity metrics specific to the identified type of exercise) or feedback (e.g., in the form of visual, audio, and/or haptic alerts) to the user and/or change/enable/disable certain functionality (e.g., turn off pedometer, change parameters of algorithms tracking certain physiological metrics (e.g., calories), etc.).

Deferred Presentation of Activity Metrics

In some cases, it may be desirable to defer the presentation of the metrics associated with a given activity. As used herein, the term "metrics," in addition to having its ordinary meaning, may be used interchangeably with "statistics" or "stats" to refer to quantifiable information associated with a given activity. For example, some activities may be difficult to detect in real-time, for example, due to the similarity of user movements performed for such activities to user movements corresponding to other activities. For such activities, rather than possibly incorrectly identifying the user's activity or presenting irrelevant activity metrics to the user in real-time, the wearable device (and/or a client device and/or a server in communications with the wearable device) may process (or complete the processing of) the activity metrics and/or present the activity metrics after the user has finished engaging in the given activity (e.g., swimming), where the activity identification and the activity metrics determination may be based on a more comprehensive set of sensor data (e.g., for the entire duration of the activity rather than just a few seconds or minutes). The techniques for both real-time and deferred processing and/or presentation of metrics are described in greater detail below with reference to FIGS. 4-11.

Wearable Device Overview

FIG. 1A is a block diagram illustrating an example wearable device in accordance with aspects of this disclosure. The wearable device 100 may include a processor 120, a memory 130, a wireless transceiver 140, and one or more sensor(s) 160. The wearable device 100 may also optionally include a user interface 110 and one or more environmental sensor(s) 150. The wireless transceiver 140 may be configured to wirelessly communicate with a client device 170 and/or server 175, for example, either directly or when in range of a wireless access point (not illustrated) (e.g., via a personal area network (PAN) such as Bluetooth pairing, via a wireless local area network (WLAN), etc.). Each of the memory 130, the wireless transceiver 140, the one or more sensor(s) 160, the user interface 110, and/or the one or more environmental sensor(s) 150 may be in electrical communication with the processor 120.

The memory 130 may store instructions for causing the processor 120 to perform certain actions. In some embodiments, the sensor(s) 160 may include one or more of biometric sensors, optical sensors (e.g., a photoplethysmographic (PPG) sensor), inertial sensors (e.g., accelerometer, gyroscope, etc.), barometric sensors (e.g., altimeter, etc.), geolocation sensors (e.g., GPS receiver), and/or other sensor(s). Further information regarding such sensors are described in more detail below (e.g., in connection with FIG. 1B).

The wearable device 100 may collect one or more types of physiological and/or environmental data from the one or more sensor(s) 160, the one or more environmental sensor(s) 150, and/or external devices and communicate or relay such information to other devices (e.g., the client device 170 and/or the server 175), thus permitting the collected data to be viewed, for example, using a web browser or network-based application. For example, while being worn by the user, the wearable device 100 may perform biometric monitoring via calculating and storing the user's step count using the one or more sensor(s) 160. The wearable device 100 may transmit data representative of the user's step count to an account on a web service (e.g., www.fitbit.com), computer, mobile phone, and/or health station where the data may be stored, processed, and/or visualized by the user. The wearable device 100 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; respiration, oxygen saturation (SpO2), blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 100 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 100 (and/or the client device 170 and/or the server 175) may collect data from the sensor(s) 160 and/or the environmental sensor(s) 150, and may calculate metrics derived from such data. For example, the wearable device 100 (and/or the client device 170 and/or the server 175) may calculate the user's stress or relaxation levels based on a combination of heart rate variability, skin conduction, noise pollution, and/or sleep quality. In another example, the wearable device 100 (and/or the client device 170 and/or the server 175) may determine the efficacy of a medical intervention, for example, medication, based on a combination of data relating to medication intake, sleep, and/or activity. In yet another example, the wearable device 100 (and/or the client device 170 and/or the server 22) may determine the efficacy of an allergy medication based on a combination of data relating to pollen levels, medication intake, sleep and/or activity. These examples are provided for illustration only and are not intended to be limiting or exhaustive.

Figure 1B:
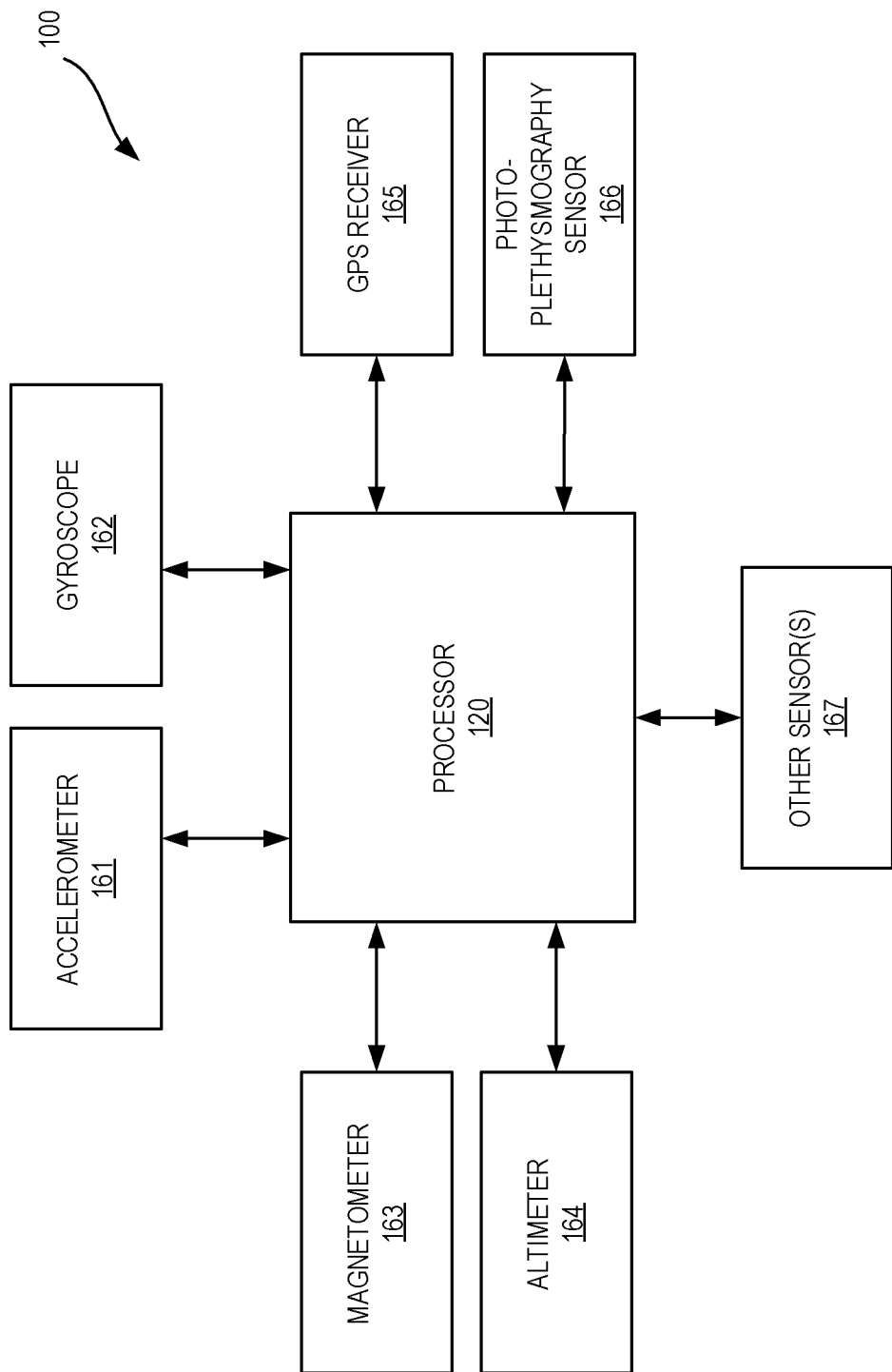
FIG. 1B is a block diagram illustrating example sensors which may be in communication with a processor of a wearable device in accordance with aspects of this disclosure.

FIG. 1B is a block diagram illustrating a number of example sensors that may be included in the wearable device 100 in accordance with aspects of this disclosure. For example, in the embodiment of FIG. 1B, the wearable device 100 includes an accelerometer 161 (e.g., a multi-axis accelerometer), a gyroscope 162, a magnetometer 163, an altimeter 164, a GPS receiver 165, a PPG sensor 166, and one or more other sensors 167 (including but not limited to, e.g., a temperature sensor, an ambient light sensor, galvanic skin response sensor, a capacitive sensor, humidity sensor, sound sensor, etc.), all of which are in communication with the processor 120. Each of the sensors illustrated in FIG. 1B may be in electrical communication with the processor 120. The processor 120 may use input received from any combination of the sensors in detecting the start of an exercise and/or in tracking the metrics for the exercise.

Although the example of FIG. 1B illustrates sensors 161-167, in other embodiments, the wearable device 100 may include a fewer number of sensors and/or any other subsets and combinations of the sensors (e.g., only the accelerometer 161, a combination of the accelerometer 161 and the gyroscope 162, etc.). The wearable device 100 may also include one or more additional sensors not illustrated in FIG. 1B.

Additionally, in some implementations, the GPS receiver 165 may be located in the client device 170 rather than the wearable device 100. In these implementations, the processor 120 may wirelessly communicate with the client device 170 to control and/or receive geolocation data from the GPS receiver 165 and/or other geolocation sensor(s).

It related aspects, the processor 120 and other component(s) of the wearable device 100 (e.g., shown in FIGS. 1A and 1B) may be implemented as any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure.

In further related aspects, the processor 120 and other component(s) of the wearable device 100 may be implemented as a System-on-Chip (SoC) that may include one or more central processing unit (CPU) cores that use one or more reduced instruction set computing (RISC) instruction sets, a GPS receiver 165, a wireless wide area network (WWAN) radio circuit, a WLAN radio circuit, and/or other software and hardware to support the wearable device 100.

Determining Location of Wearable Device

Figure 1C:
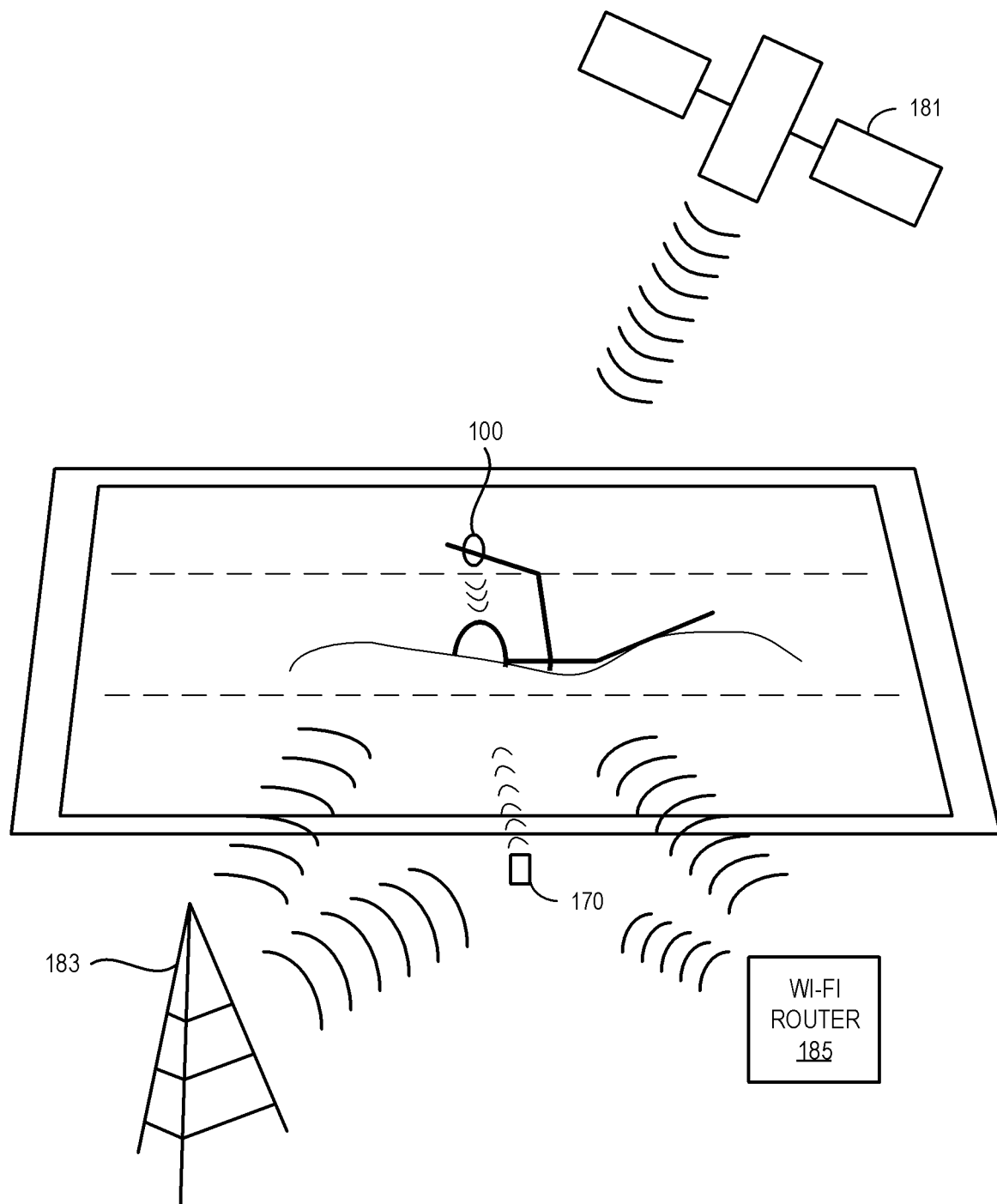
FIG. 1C is an example block diagram illustrating a number of geolocation sensors that may be used in determining the location of the wearable device in accordance with aspects of this disclosure.

FIG. 1C is an example block diagram illustrating geolocation sensor(s) that may be used in determining the location of the wearable device in accordance with aspects of this disclosure. As shown in FIG. 1C, a user is wearing a wearable device 100 on his/her wrist while swimming in a swimming pool. The user's client device 170 is placed next to the swimming pool. A given geolocation sensor (e.g., the GPS receiver 165) of the wearable device 100 and/or the client device 170 may receive geolocation data from a GPS satellite 181. Although only one GPS satellite 181 is illustrated in FIG. 1C, the geolocation sensor may receive data from a plurality of GPS satellites at one time, typically three or more GPS satellites.

The geolocation sensor(s) (e.g., WWAN and/or WLAN radio component(s) in the wearable device 100 and/or the client device 170) may also receive geolocation data from a cellular base station 183 and/or a Wi-Fi router 185. Those skilled in the art will recognize that the geolocation sensor(s)

may be able to determine the location of the wearable device 100 based on information received from the cellular base station 183 and/or the Wi-Fi router 185. For example, the cellular base station 183 may include geolocation data in the communications with the wearable device 100 and/or the client device 170 or may provide the wearable device 100 and/or the client device 170 with a unique identifier that identifies the cellular base station 183. Thus, a given geolocation sensor may be able to determine the location of the cellular base station 183 based on the unique identifier and retrieve the corresponding location from a memory 130 or from a server 175 (which may be connected to the wearable device 100 and/or the client device 170 via the Internet). The geolocation sensor may also be able to infer the distance of the wearable device 100 from the cellular base station 183 based on the strength of the signal received therefrom. The geolocation sensor may also be able to estimate the location of the wearable device 100 based on triangulation techniques with three or more cellular base stations 183.

The geolocation sensor(s) may also be able to determine the location of the wearable device 100 based on data received from the Wi-Fi router 185. The determination of the location of the wearable device 100 based on the data from the Wi-Fi router 185 may be similar to the techniques used for determining location based on the data received from the cellular base station 183. For example, a given geolocation sensor may receive a unique identifier (e.g., an Internet Protocol (IP) address, Service Set Identifier (SSID), etc.) from the Wi-Fi router 185 based on which the geolocation sensor may look up the location of the Wi-Fi router 185. Additionally, the geolocation sensor may refine the geolocation data received from the Wi-Fi router 185 based on the strength of the received Wi-Fi signal, which may be related to the distance of the wearable device 100 from the Wi-Fi router 185.

Based on the determined location of the wearable device 100, the wearable device 100 and/or the client device 170 may determine whether the user is (or was) in or near a body of water (e.g., swimming pool, lake, ocean, etc.). The information regarding whether the user is (or was) in or near a body of water may be used by the wearable device 100 and/or the client device 170 for determining whether the user is (or was at a specific period of time in the past) swimming. In one example, based on a determination that the user is in or near a body of water and a determination that the sensor data generated by the one or more sensors provided on the wearable device 100 indicates that the user is likely to be swimming, the wearable device 100 may begin collecting swim metrics. As used herein, the term "collect," in addition to having its ordinary meaning, may be used interchangeably with "determine," "extract," "calculate," "generate", etc. to refer to the steps performed to arrive at the desired data (e.g., swim metrics).

In another example, based on a determination that the user is in or near an open lake, river, or ocean, the wearable device 100 may determine that the user is engaged in open-water swimming and/or begin collecting open-water swim metrics. Upon determining that the user is (or was) engaged in each of open-water swimming, biking, and running, the wearable device 100 may determine and present triathlon metrics in a triathlon user interface. For example, based on the determination that the user is (or was) engaged in each of open-water swimming, biking, and running, the wearable device 100 may present triathlon metrics to the user without receiving an input from the user indicating that the user is (or has finished) participating in a triathlon. Alternatively, the wearable device 100 may receive an input from the user indicating that the user is (or has finished) participating in a triathlon, and automatically detect the open-water swimming portion of the triathlon based on the location of the wearable device 100 being in or near an open lake, river, or ocean, as described above. Based on such detection, the wearable device 100 may present (e.g., either during open-water swimming portion of the triathlon or after the open-water swimming portion of the triathlon has finished) swim metrics to the user.

In another example, based on a determination that the user is (or was) in or near a body of water and a determination that the sensor data generated by the one or more sensors provided on the wearable device 100 includes a pattern of stroke-like (or kick-like) movements, the client device 170 may identify the time periods corresponding to such determinations as swim periods. In yet another example, based on a determination that the user is (or was) in or near a body of water, the wearable device 100 and/or the client device 170 may retrieve additional information regarding the body of water (e.g., swimming pool length, etc.) and use the additional information to provide additional metrics (e.g., swim speed calculated by swimming pool length divided by lap duration).

In related aspects, the processor(s) 120 of the wearable device 100 (and/or the processor(s) on the client device 170 paired with the wearable device 100) may determine the availability and reliability of geolocation data from the GPS receiver 165 and/or the other geolocation sensor(s), and select a subset or portion of the geolocation data to use in determining the geolocation of the wearable device 100. In further related aspects, the processor(s) 120 of the wearable device 100 (and/or the processor(s) on the client device 170) may aggregate the geolocation data from GPS receiver 165 and/or the other geolocation sensor(s), and may determine the geolocation of the wearable device 100 based on the aggregated geolocation data.

Measuring Heart Rate, Heart Rate Variability, and/or Other Related Metrics

Figure 1D:
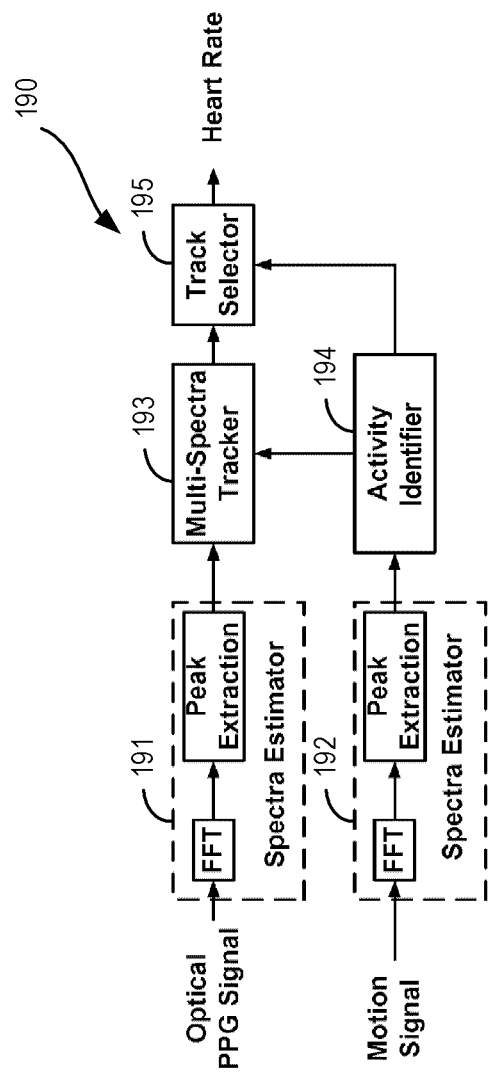
FIG. 1D is an example block diagram of a system used for determining a heart rate in accordance with aspects of this disclosure.

FIG. 1D is an example block diagram of a system used for determining heart rate in accordance with aspects of this disclosure. As shown in FIG. 1D, the wearable device 100 may include a system 190 of circuit components for determining the heart rate of the user based on an optical PPG signal (e.g., received from the PPG sensor 166 of FIG. 1B) and a motion signature (e.g., received from the accelerometer 161 of FIG. 1B). As used herein, a motion signature may refer to any biometric signature or signal that may be received from and/or based on output data from one or more of sensors, such as, for example, inertial sensor(s) (e.g., accelerometer(s) and gyroscope(s)), barometric sensors(s) (e.g., altimeter(s)), which may be indicative of the activity and/or physiological state of a user of the wearable device 100. The system 190 may be implemented by hardware components and/or in software executed by the processor 120. The system 190 may include first and second spectra estimators 191 and 192, a multi-spectra tracker 193, an activity identifier or discriminator 194, and a track selector 195. Each of the first and second spectra estimators 191 and 192 may include a Fast Fourier Transform (FFT) block and a peak extraction block. In the example of FIG. 1D, the activity identifier 194 may use the peaks extracted from the motion signature to determine the activity that the user is performing (e.g., sedentary, walking, running, sleeping, lying down, sitting, biking, typing, elliptical, weight training, swimming, etc.). This determination of the current activity of the user may be used by the multi-spectra tracker 193 and the track selector 195 in extracting the heart rate from the optical PPG signal. Thus, the motion signature in FIG. 1D may be used by the system 190 to determine the current activity of the user. In other embodiments, the processor 120 may use a similar technique to the activity identifier 194 in determining the type of an exercise, as discussed in greater detail below.

The blocks illustrated in FIG. 1D are merely examples of components and/or processing modules that may be performed to supplement a PPG signal with a motion signature to determine heart rate. However, in other implementations, the system 190 may include other blocks or may include input from other biometric sensors of the wearable device 100.

Under certain operating conditions, the heart rate of the user may be measured by counting the number of signal peaks within a time window or by utilizing the fundamental frequency or second harmonic of the signal (e.g., via an FFT). In other cases, such as heart rate data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signature and the output may be used to perform activity discrimination which may be used to assist the multi-spectra tracker 193. For instance, it may be determined that the user was stationary and has begun to move. This information may be used to by the multi-spectra tracker 193 to bias the track continuation toward increasing frequencies. Similarly, the activity identifier 194 may determine that the user has stopped running or is running slower and this information may be used to preferentially bias the track continuation toward decreasing frequencies.

Tracking may be performed by the multi-spectra tracker 193 with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 195 may use the output tracks from the multiple-spectra tracker 193 and estimate the user's heart rate based on the output tracks. The track selector 195 may estimate a probability for each of the tracks that the corresponding track is representative of the user's heart rate. The estimate may be taken as the track having the maximum probability of being representative of the user's heart rate, a sum of the tracks respectively weighted by their probabilities of being representative of the user's the heart rate, etc. The activity identifier 194 may determine a current activity being performed by the user which may be used by the track selector 195 in estimating the user's heart rate. For instance, when the user is sleeping, sitting, lying down, or sedentary, the user's estimated heart rate may be skewed toward heart rates in the 40-80 bpm range. When the user is running, jogging, or doing other vigorous exercise, the user's estimated heart rate may be skewed toward elevated heart rates in the 90-180 bpm range. The activity identifier 194 may determine the user's current activity (e.g., a current exercise) based at least in part on the speed of the user. The user's estimated heart rate may be shifted toward (or wholly obtained by) the fundamental frequency of the selected output track when the user is not moving. The output track that corresponds to the user's heart rate may be selected by the track selector 195 based on criteria that are indicative of changes in activity. For instance, when the user begins to walk from being stationary, the track selector 195 may select the output track that illustrates a shift toward higher frequency based on output received from the activity discriminator 194.

Although some embodiments of the present disclosure are described with respect to heart rate, the techniques described herein may be extended to other metrics. For example, sensor data generated by the one or more sensors described herein may be used to determine respiration, SpO2, blood volume, blood glucose, skin moisture, and skin pigmentation level and, for example, utilize such metrics for activity detection/identification.

Perspective Views of Example Wearable Device

Figure 2:
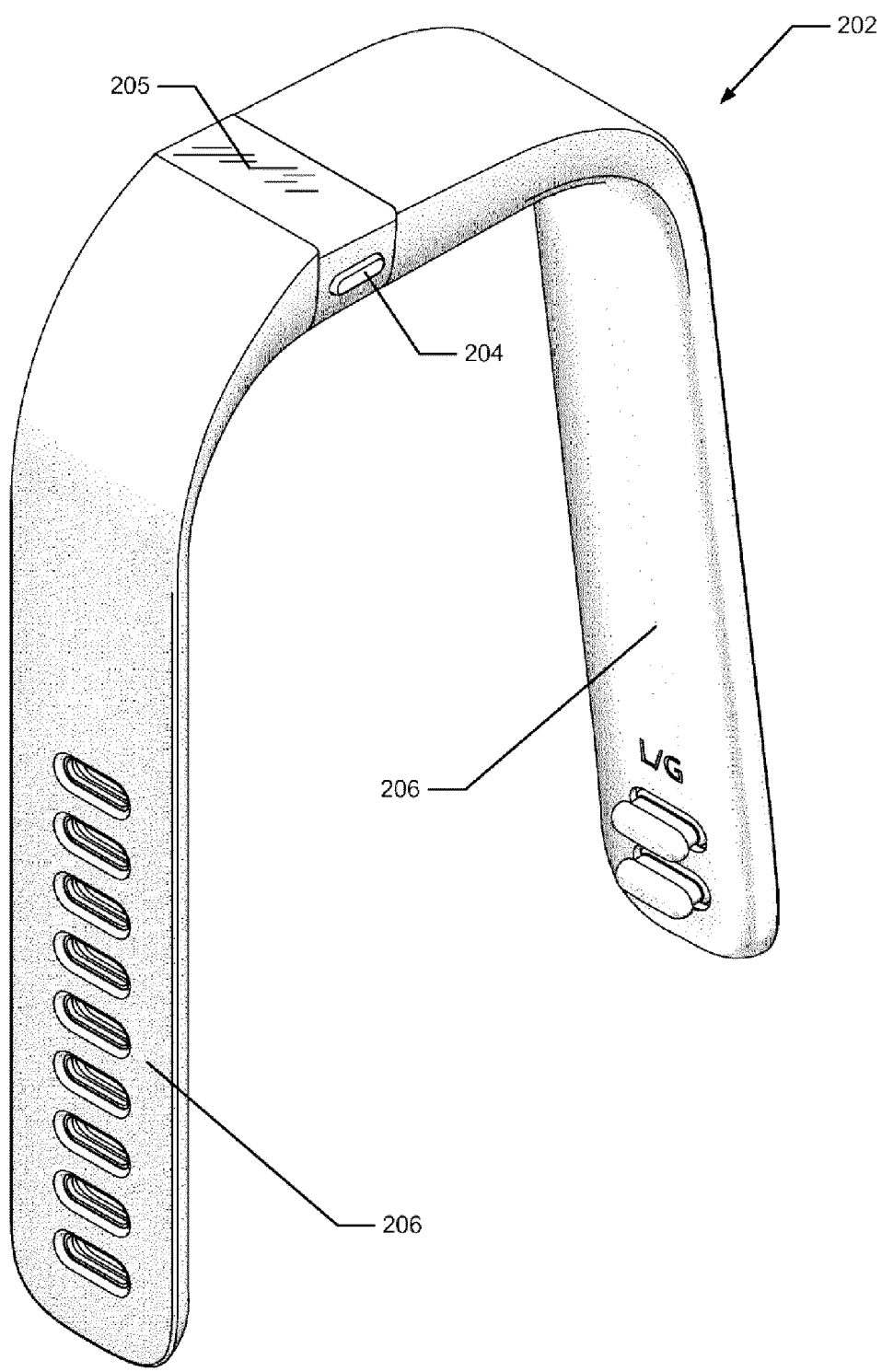
FIG. 2 is an example of a wrist-worn device in accordance with aspects of this disclosure.

The wearable device 100 according to embodiments and implementations described herein may have a shape and/or size adapted for coupling to (e.g., secured to, worn, borne by, etc.) the body or clothing of a user. FIG. 2 shows an example of a wrist-worn wearable device 202 in accordance with aspects of this disclosure. The wrist-worn wearable device 202 may have a display 205, button(s) 204, electronics package (not illustrated), and/or an attachment band 206. The attachment band 206 may be secured to the user through the use of hooks and loops (e.g., Velcro), a clasp, and/or a band having memory of its shape, for example, through the use of a spring metal band.

Figure 3:
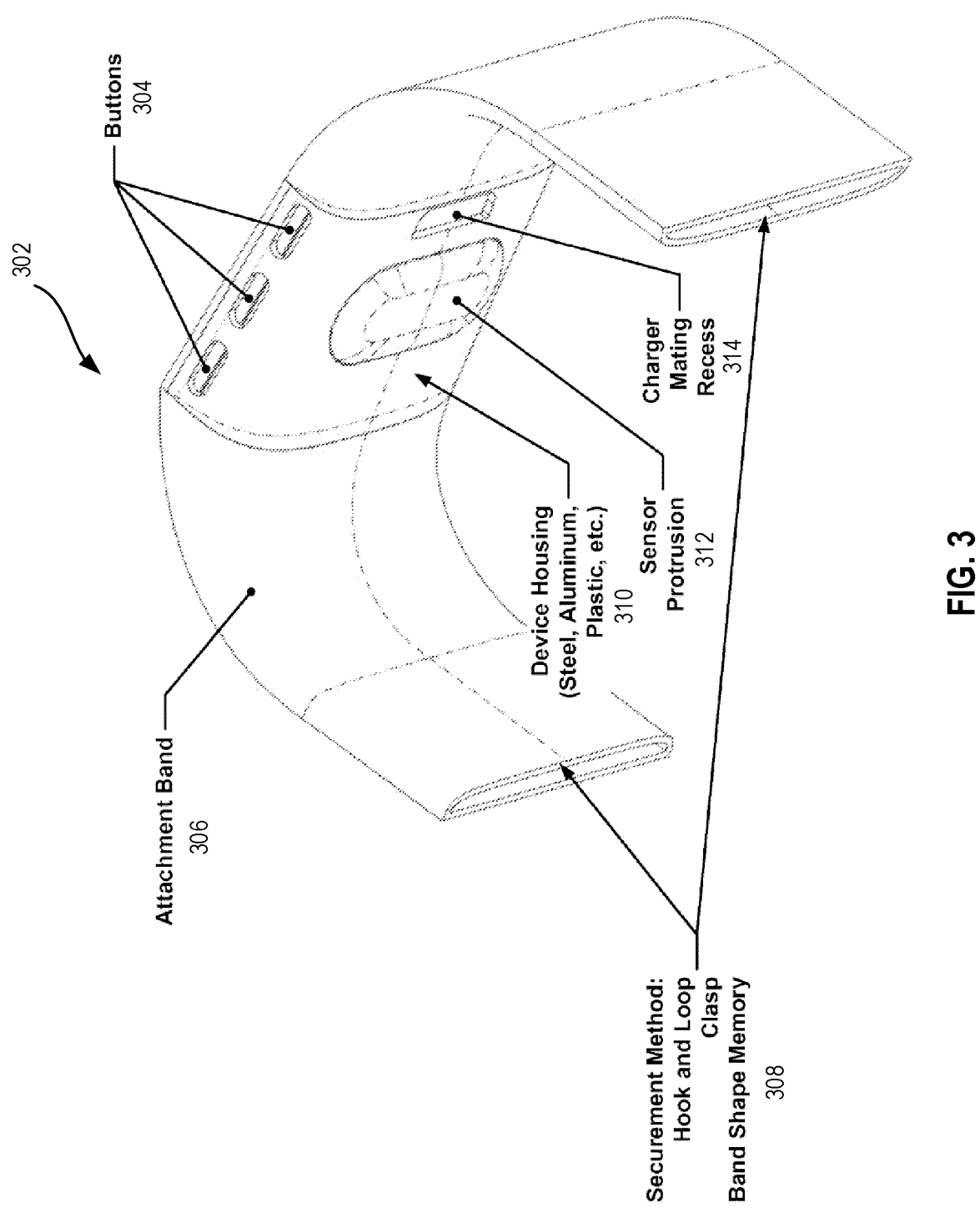
FIG. 3 is a perspective view illustrating another example of a wrist-worn device in accordance with aspects of this disclosure.

FIG. 3 is a perspective view illustrating another example of a wrist-worn device in accordance with aspects of this disclosure. The wrist-worn wearable device 302 of FIG. 3 may include button(s) 304, an attachment band 306, fasteners 308 (e.g., hook and loops, clasps, or band shape memory), a device housing 310, a sensor protrusion 312, and/or a charging/mating recess 314 (e.g., for mating with a charger or data transfer interface of a cable, etc.). One or more components of the wearable device 302 may be waterproof or water-resistant. In some embodiments, one or more additional elements may be provided for waterproofing the wearable device 302 and/or component(s) thereof. For example, a waterproof cover may be provided to protect such component(s) (e.g., the charging/mating recess 314) from water. In contrast to the wrist-worn wearable device 202 of FIG. 2, in FIG. 3, the wrist-worn wearable device 302 includes the sensor protrusion 312 and the recess 314 for mating with a charger and/or data transmission cable. FIG. 3 also illustrates the device housing 310 which may house internals of the wrist-worn wearable device 302 such as, for example, the processor 120, and the one or more sensors illustrated in FIG. 1B. For example, one or more optical sensors (e.g., the PPG sensor 166) may be housed directly below the sensor protrusion 312. Although a wrist-worn device is illustrated in the example of FIG. 3, the embodiments of this disclosure are not limited as such, and the wearable devices described herein may include wearable devices other than wrist-worn devices, such as those worn on other parts of the body.

Automatic Detection and Tracking of Exercises

Certain aspects of this disclosure relate to the automatic detection and tracking of exercises, more specifically swimming. As described above, one application for a wearable device, such as the wearable device 100, is the tracking of exercises performed by a user of the wearable device 100. While a user may manually start and/or end the tracking of an exercise, which may involve the selection of the exercise to be performed, along with the optional selection of goals such as a target heart rate, distance, exercise time period, etc., the techniques described herein may allow a user to start and/or end an exercise without manual input or interaction with the wearable device 100, and the wearable device 100 may be able to automatically start and/or stop the tracking of the exercise. This may allow the user to skip the input of start and/or end of the exercise and/or the other parameters and still have the exercise be tracked by the wearable device 100.

In some cases, automatic detection of activities may result in possibly incorrect activity identification (e.g., due to the similarity of user movements among multiple activities). For example, if the wearable device determines that the user has started swimming when the user is actually stretching, the wearable device may begin displaying or surfacing swim-specific metrics such as lap counts and stroke counts, negatively affecting the user's experience with the wearable device. To reduce or eliminate such potential false positives, one or more activities may be reserved for identification after the fact (e.g., after the user has finished performing the activity). For example, the wearable device (and/or a client device and/or a server in communications with the wearable device) may process (or complete the processing of) the activity metrics and/or present the activity metrics after the user has finished engaging in the given activity (e.g., swimming). The metrics relevant to such activities may be presented to the user after the user has finished performing the activity, via a mobile application executing on the user's mobile device, via a website associated with the wearable device, and/or via a display screen (e.g., viewable by the user and/or others) connected to a computing device in communication with the wearable device and/or the user's mobile device. For example, the display screen may be part of a mobile device, a standalone display unit at the swim site (e.g., pool or aquatics center), etc.

Swim Metrics

In certain embodiments, wearable devices may provide swim metrics such as lap count and stroke count based on sensor data generated by one or more sensors within the wearable devices. Some of such devices utilize a manual input from the user indicating that the user has begun or finished swimming before they begin tracking swim metrics. For example, before the user begins swimming, he or she may press a start button on the wearable device to indicate that the user is about to begin swimming. The wearable device may then begin tracking various swim metrics such as lap count, lap time, stroke count, stroke type, etc. Once the user is done, he or she can press an end button to indicate that the user has finished swimming. The wearable device may then present the user with a summary of the swim session.

Automatic Detection and Quantification of Swimming

As discussed above, in some embodiments, wearable devices may track an activity only after the user has manually activated tracking of the activity. For example, in such devices, swim metrics may be collected and presented to the user after the user has activated the swim metrics tracking function of the wearable device (e.g., through an on-device interface or a companion mobile application). However, the user may forget to enable or activate the activity metrics tracking function prior to engaging in an activity. In such cases, the user may be disappointed to find out that his or her workout session was not monitored by the wearable device. Thus, a method of presenting activity metrics to the user that does not require a manual input from the user is desired.

According to embodiments of the present disclosure, swim metrics may be collected without any user input (e.g., user input indicating that the user is swimming, has begun swimming, or has finished swimming). Further, swim periods (e.g., periods during which the user is likely to have been swimming) may be identified without any user input (e.g., user input indicating that the user is swimming, has begun swimming, or has finished swimming). These embodiments are described in greater detail below with reference to FIGS. 4-11.

Example Swim Detection

A wearable device (e.g., the wearable device 100) may determine, based on the output of one or more sensors (e.g., the sensor(s) 160), that a user of the wearable device has started an activity. Then, the wearable device may identify the type of activity based on comparing the output of the one or more sensors to predefined rules or thresholds corresponding to a plurality of activities (e.g., an exercise such as swimming or a non-exercise activity such as sleeping). In response to identifying the type of activity performed by the user, the wearable device may communicate activity-specific metrics to the user via the wearable device, a mobile device in communication with the wearable device, and/or another computing device in communication with the wearable device and/or the mobile device. The activity metrics may be displayed or surfaced on the display screen of such devices. In some embodiments, in response to identifying the type of activity performed by the user, the wearable device may provide feedback (e.g., in the form of visual, audio, and/or haptic alerts) to the user via the wearable device, a mobile device in communication with the wearable device, and/or another computing device in communication with the wearable device and/or the mobile device.

Swim Metrics Tracking

A wearable device (e.g., the wearable device 100) may collect swim metrics based on the user's movement. For example, if the wearable device determines that the user's movement is similar (based on sensor data) to a swim stroke (and/or kick), the wearable device may determine that the user has performed a swim stroke (and/or kick). The wearable device may determine whether a user's movement (and/or series of movements) is similar to a given movement associated with an activity by comparing the sensor data generated by one or more sensors on the wearable device to a plurality of rules maintained for each activity. In the swimming example, the wearable device may maintain a set of rules for detecting a lap and a swim stroke and for identifying the stroke type (e.g., freestyle, butterfly, breaststroke, backstroke, etc.). The wearable device may also determine the time at which the laps and swim strokes are taking place in order to calculate the lap times (e.g., start, end, duration, etc.). The swim metrics collected by the wearable device may further include swim speed (e.g., determined based on information about the size of the pool) and estimated number of calories burned.

Sensor(s) Used For Swimming Metrics Tracking

The wearable device 100 may determine the swim metrics based on sensor data generated by one or more sensors of the wearable device. For example, the sensors used for generating the sensor data may include one or more of inertial sensors (e.g., accelerometer(s) and/or gyroscope(s)) and barometric sensors (e.g., altimeter(s)). In some embodiments, the wearable device determines the swim metrics by extracting features from the sensor data and using the extracted features to determine the number of strokes, the type of strokes, the lap start time, the lap end time, the lap duration, etc.

Timing of Collecting Swim Metrics

In some embodiments, the wearable device 100 collects swim metrics regardless of whether the person is determined to be swimming or not. In one example, the device collects swim metrics during one or more periods of time or for an extended period of time (e.g., all day) without determining whether the user's swimming or not. In another example, the device collects swim metrics only upon determining that the user is active. In yet another example, the device collects swim metrics only upon determining that the user is near a body of water (e.g., swimming pool, ocean, lake, etc.). In such an example, the device can determine whether the user is near a body of water (e.g., within a threshold distance) based on GPS data, as described with reference to FIG. 1C. In yet another example, the device collects swim metrics only upon determining that the user is swimming. In yet another example, the device collects swim metrics only upon determining that any one of the combinations of conditions described in this paragraph is satisfied (e.g., user is active and near a body of water, user is determined to be swimming and near a body of water, etc.).

Example Method for Collecting Swim Metrics

Figure 4:
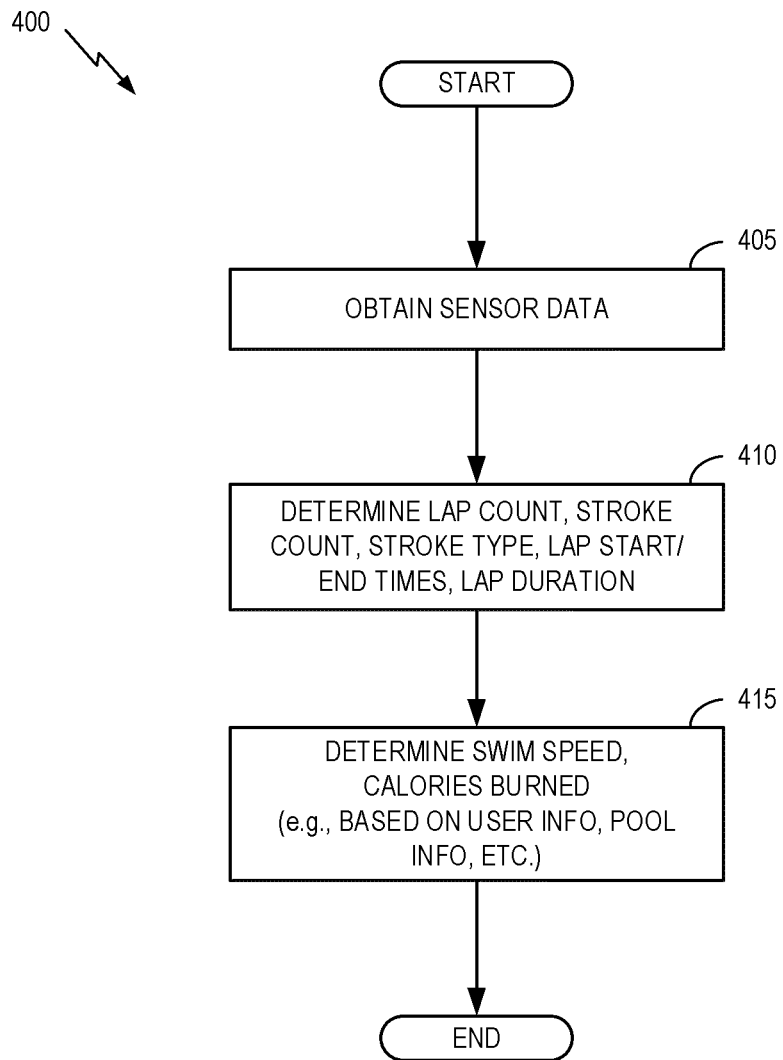
FIG. 4 is a flowchart illustrating an example method for collecting swim metrics in accordance with aspects of this disclosure.

FIG. 4 is a flowchart illustrating an example method for collecting swim metrics in accordance with aspects of this disclosure. The method 400 may be operable by a wearable device 100, or component(s) thereof, for collecting swim metrics or any other activity metrics in accordance with aspects of this disclosure. For example, the steps of method 400 illustrated in FIG. 4 may be performed by a processor 120 of the wearable device 100. In another example, a client device 170 (e.g., a mobile phone) or a server 175 in communication with the wearable device 100 may perform at least some of the steps of the method 400. For convenience, the method 400 is described as being performed by the processor 120 of the wearable device 100.

At block 405, the processor 120 obtains sensor data. As described herein, the sensor data may be generated by one or more sensors provided on the wearable device 100. In some embodiments, the processor 120 may further process the obtained sensor data. Such processing may include extraction of features relevant to the given activity, such as swimming.

At block 410, the processor 120 determines lap count, stroke count, stroke type, lap start/end times, and/or lap duration. For example, the processor 120 may identify strokes by counting the number of acceleration peaks extracted from the sensor data. Further, the processor 120 may identify the start of a lap and the end of a lap by determining whether a break between the acceleration peaks span a threshold time period (e.g., a threshold number of seconds, or a value that is greater than the average break between strokes by a threshold value). In another example, the processor 120 may identify the start of a lap and the end of a lap by determining whether there is an acceleration peak having a magnitude that is greater than (or less than) the average magnitude of the acceleration peaks. In some embodiments, the processor 120 collects the swim metrics (e.g., lap count, stroke count, stroke type, lap start/end times, lap duration, etc.) without determining whether the sensor data indicates that the user is likely to be swimming (or without receiving an indication that the user is likely to be swimming). As another example, the processor 120 may identify the start of a lap and the end of a lap by determining whether the sensor data (e.g., from inertial and/or barometric sensor(s)) is indicative of the user performing a swimming turn (e.g., open turn, tumble/flip turn, backwards flip turn, etc.).

At block 415, the processor 120 determines additional information such as swim speed and/or calories burned. To calculate the swim speed, the processor 120 may access (or request from the user or other database) additional information such as the pool size or length, degree of stillness/waves in pool, and/or other data about the swim location (e.g., average degree of crowdedness at the pool during a given time period). To calculate the calories burned, the processor 120 may access (or request from the user or other database) additional information about the user (e.g., age, weight, height, etc.).

In the method 400, one or more of the blocks shown in FIG. 4 may be removed (e.g., not performed) and/or the order in which the method is performed may be switched. For example, in some embodiments, one or more of blocks 405, 410, and 415 may be omitted. In some embodiments, the blocks 410 and 415 may be switched. In some embodiments, additional blocks may be added to the method 400. The embodiments of the present disclosure are not limited to or by the example shown in FIG. 4, and other variations may be implemented without departing from the spirit of this disclosure.

Swim Period Identification

The wearable device 100 can identify periods of swimming based on the sensor data. For example, the wearable device may analyze overlapping windows of time in the sensor data to determine which activity the user is performing at any given time period. In some embodiments, the wearable device compares the sensor data to the rules and thresholds corresponding to a plurality of activities. Based on the comparison, the wearable device may identify a single activity that the user is most likely to be performing at any given moment. In some of such embodiments, the wearable device extracts various features from the sensor data, compares the extracted features to the known features corresponding to the plurality of activities, and identifies an activity with features having the strongest correlation with the features extracted from the sensor data.

Extracted Features

Features extracted from the sensor data may comprise various indicators used for classifying the activity performed by the user as one of a plurality of activities (e.g., walking, running, swimming, sleeping, etc.). These features may be extracted from each overlapping window of time, where each overlapping window of time includes a number of samples (e.g., sensor readings). In some embodiments, the extracted features include one or more of the mean of the samples, the standard deviation of the samples, and the energy of the samples. The extracted features may be further processed and compared against a set of threshold values for a variety of activities, such as, for example, swimming.

Location of Swim Period Identification

Although the swim period identification is described as being performed by the wearable device (e.g., the wearable device 100) in some embodiments described herein, the swim period identification can also be performed by a mobile device (e.g., the client device 170) of the user (e.g., paired or otherwise in communication with the wearable device) or another computing device capable of communicating with such a mobile device or to the wearable device, such as the server 175. For example, in some embodiments, the identification of swim periods is performed by the smartphone or other mobile device that can wirelessly connect to the wearable device. In other embodiments, the identification of swim periods is performed by a server that can communicate with the smartphone or other such mobile devices (and/or directly with the wearable device) over a network (e.g., Internet).

Swim Period Identification By Wearable Device

If the identification of swim periods is performed by the wearable device 100, upon the identification of a swim period, the wearable device can perform a variety of additional tasks such as begin tracking swim metrics, launch the swim application, toggle swim mode, turn on additional sensors for providing more advanced swim metrics, etc. These additional tasks are described in greater detail below with reference to FIG. 11.

Advantageously, by performing these additional tasks only upon the identification of a swim period (e.g., detection that the user has begun swimming), power savings can be achieved. For example, in some embodiments, the wearable device may collect swim metrics only when the device determines that the user is swimming. In such embodiments, the wearable device stops collecting swim metrics in response to a determination that the user is no longer swimming.

Swim Period Identification By Mobile Device

In some embodiments, the identification of swim periods occurs on a mobile device (e.g., the client device 170) that can communicate with the wearable device. For example, the sensor data collected by the wearable device may be sent (with or without additional processing by the wearable device) to such a mobile device of the user, and the mobile device can analyze the sensor data to identify the periods during which the user is likely to have been swimming.

Advantageously, identification of swim periods on such a mobile device can provide the power savings for the wearable device (e.g., since identification is not performed by the wearable device), without requiring the infrastructure of a centralized database.

Swim Period Identification By Centralized Server

In some embodiments, the identification of swim periods occurs on a centralized server (e.g., the server 175) that can communicate with the wearable device and/or the mobile device of the user. For example, the sensor data collected by the wearable device may be sent (with or without additional processing by the wearable device) to such a server (either directly or via the mobile device), and the server can analyze the sensor data to identify the periods during which the user is likely to have been swimming.

Advantageously, identification of swim periods on such a centralized server can provide the power savings for the wearable device (e.g., since identification is not performed by the wearable device).

Timing of Identification: After Conclusion of User Activity (Post-Activity)

If the identification is performed by the wearable device after the fact (e.g., not while the user is still engaging in the activity, but after the user has finished the activity), the wearable device identifies (or attempts to identify) swim periods after a threshold time period has passed since the most recent identification of swim periods (e.g., hourly, daily, after a certain time period has passed, at most once every hour, at most once every day, etc.).

If the identification is performed by an entity other than the wearable device, in some embodiments, upon determining that sensor data (or other processed data) is received (e.g., by syncing such data) from the wearable device, such an entity (e.g., mobile device, server, etc.) identifies the swim periods based on the received data. In one example, the entity identifies (or attempts to identify) swim periods every time sensor data is received from the wearable device. In another example, the entity identifies (or attempts to identify) swim periods after a threshold time period has passed since the most recent identification of swim periods (e.g., hourly, daily, after a certain time period has passed, at most once every hour, at most once every day, etc.).

Timing of Identification: In Real-Time

In some embodiments, the wearable device periodically determines whether the sensor data indicates that the user is swimming. For example, the wearable device may process each overlapping window of time to determine whether the sensor data corresponding to a given overlapping window indicates that the user is swimming.

In some embodiments, the amount of sensor data used for real-time identification is different from the amount of sensor data used for post-activity identification. For example, real-time identification may be based on sensor data corresponding to a shorter time period (e.g., seconds, minutes, etc.) than the time period corresponding to the sensor data used for post-activity identification (e.g., all available sensor data, such as sensor data for a full day or other extended time period).

Thus, post-activity identification of swim periods may be based on more complete information (e.g., sensor data encompassing the entire time period during which the user is engaged in a given activity) and does not have the same time constraints of real-time identification, in which case the wearable device may need to identify the activity and begin presenting live data to the user within seconds or minutes. In some embodiments, the algorithm used for real-time identification of swim periods is different from the algorithm used for post-activity identification of swim periods.

In some embodiments, real-time identification of swim periods can compensate for the limited time period within which to collect and process data from basic sensors (e.g., accelerometer) by activating additional sensors (e.g., gyroscope(s), magnetometer(s), altimeter(s), etc.). For example, if the wearable device 100 determines, based on preliminary sensor data, that the user may be swimming, the wearable device 100 may cause one or more additional sensors to be activated and make a more accurate determination of whether the user is swimming or not, as described in further detail below with reference to block 1160 (and the sub-blocks contained therein) of FIG. 11.

Combination of Identifications

In some embodiments, both real-time identification and post-activity identification are performed. In one example, the real-time identification is performed by the wearable device, and the post-activity identification is performed by a mobile device or a centralized server. In another example, both the real-time identification and the post-activity identification are performed by the wearable device.

In some embodiments, only post-activity identification is performed (e.g., without using real-time identification). In such embodiments, the user may be presented with swim metrics only after the user has finished swimming.

In some embodiments, only real-time identification is used (e.g., without using post-activity identification). In some of such embodiments, the user may be presented with swim metrics only during the swimming session. Alternatively, the user is presented with swim metrics during the swimming session as well as after the user has finished swimming.

Use of Geolocation Data in Swim Period Identification

In some embodiments, the wearable device (or another entity such as the mobile device) can determine whether the user is near a body of water based on geolocation data (e.g., GPS data), as described with reference to FIG. 1C. In one example, the device performing the swim period identification may eliminate, after identifying swim periods, those the identified swim periods that do not correspond to the time periods during which the user is determined to be near a body of water based on the geolocation data. In another example, the device performing the swim period identification identifies swim periods based on only a portion of the sensor data corresponding to the time periods during which the user is determined to be near a body of water based on the geolocation data.

Post-Activity Swim Period Identification and Swim Metrics Tracking

In some embodiments, post-activity identification of a swim period facilitates the use of fewer and/or less power hungry sensor(s) (e.g., to track swim metrics while the user is performing the activity and/or to identify the swim periods), as well as reduced data collection and analysis within a time period. For example, in view of the post-activity identification, the wearable device may not need to distinguish a swim stroke from the user stretching his arms. Thus, the wearable device may count any user movement that is remotely similar to a swim stroke as a swim stroke without having to establish complicated sensor data rules that would only be satisfied by a swim stroke as opposed to other user movements or carve out specific exceptions for other user movements.

Swimming vs. Other User Activities

In some embodiments, the wearable device (or other entity performing the swim period identification) can determine whether the sensor data indicates that the user activity performed at any given moment is swimming or not. In some of such embodiments, the device determines whether the sensor data satisfies one or more rules indicative of whether the user is swimming (e.g., "is this swimming?").

In other embodiments, the wearable device (or other entity performing the swim period identification) can determine whether the sensor data indicates that the user activity performed at any given moment is swimming or a user activity other than swimming (e.g., running, walking, sleeping, etc.). In some of such embodiments, the device identifies, for each given time period, the activity that most closely matches the sensor data (e.g., whether the activity data is more indicative of swimming than running).

Identification Without User Input

The techniques described herein allow identification of swim periods and presentation of swim metrics without requiring the user to provide an indication that the user has begun swimming or finished swimming. In one example, the wearable device (or other entity performing the swim period identification) determines that the user is swimming without a manual activation by the user. In another example, the device identifies swim periods without a user input indicative of the start or end of the user's swim session. In yet another example, the device identifies swim periods without taking into account any input via the user interface provided on the wearable device or another mobile device of the user (e.g., buttons, touch screens, etc.).

Sensors Used For Swim Period Identification

The identification of swim periods can be performed based on sensor data generated by a variety of sensors. In one example, swim periods are identified based only on the sensor data generated by an accelerometer provided on the wearable device. In another example, swim periods are identified based on the sensor data generated by the accelerometer and one or more additional sensors (e.g., magnetometer, altimeter, gyroscope, GPS receiver, optical sensor used for determining a heart rate and other related metrics described herein, etc.).

In some embodiments, the number and type of sensors used for identifying the swim periods differ based on whether the identification is made in real-time and/or after the fact. For example, for post-activity identification, only the accelerometer data may be used, whereas for real-time identification, the accelerometer data and additional sensor data (e.g., data generated by one or more sensors described herein such as magnetometer, altimeter, gyroscope, GPS receiver, optical sensor, or another combination of sensors described) may be used. In some embodiments, both post-activity identification and real-time identification are performed, and the post-activity identification is performed based only on the sensor data generated by an accelerometer, and the real-time identification is performed based on sensor data generated by accelerometer and one or more additional sensors (e.g., magnetometer, altimeter, gyroscope, GPS receiver, optical sensor, etc.).

In some embodiments, the post-activity identification is performed based on sensor data generated by a 3-axis inertial-measurement unit (IMU), and the real-time identification is performed based on sensor data generated by a 6-axis IMU or a 9-axis IMU. For example, the 3-axis IMU may be an accelerometer, the 6-axis IMU may be a combination of an accelerometer and a gyroscope, and the 9-axis IMU may be a combination of an accelerometer, a gyroscope, and a magnetometer. In some embodiments, lower-power sensors such as an accelerometer or altimeter are used to produce a preliminary or lower-confidence real-time identification of swimming activity, upon which higher-power sensors (e.g., 9-axis IMU sensors) may be briefly toggled on to confirm or improve the confidence in the lower-confidence real-time swim identification.

In some embodiments, each movement measure may be a single numeric value generated based on a combination (e.g., addition, average, and/or the like) of a quantification of a distribution of the motion data along one or more axes of the motion sensor (e.g., a multi-axis IMU). The single numeric number may be a compact representation of the user's motion and may be used to detect user's activity (e.g., swimming).

Using the movement measure, quantified at one or more defined intervals or frequencies, informative statistical metrics may be generated by one or more component(s) of the wearable device 100 (and/or the client device 170 and/or the server 175) to characterize a user's movements. For example, the generated metric may quantify the distributions of acceleration data along axes and combine them into a single numeric number. Let $a\_x$, $a\_y$, $a\_z$ represent time series arrays of accelerometer data measured along three axes sampled at a defined sampling rate over a defined interval of time.

One embodiment of the movement measure uses the maximum and minimum acceleration along an axis to quantify the distribution of acceleration along that axis. The separate values from each axis are summed together into a single metric for each defined time interval. For example, the movement measure (MM) generated from a set of motion data generated over a time period may then be expressed according to equation (1):

$$MM = \max(a\_x) - \min(a\_x) + \max(a\_y) - \min(a\_y) + \max(a\_z) - \min(a\_z) \quad (1)$$

A more general form of this metric allows for different weighting along different axes and different exponential powers for each axis. $w\_x$, $w\_y$, $w\_z$ are weighting factors and $\exp\_x$, $\exp\_y$, $\exp\_z$ are exponents. The movement measure may be expressed according to equation (2):

$$MM = w\_x * (\max(a\_x) - \min(a\_x))^{\exp\_x} + w\_y * (\max(a\_y) - \min(a\_y))^{\exp\_y} + w\_z * (\max(a\_z) - \min(a\_z))^{\exp\_z} \quad (2)$$

It is to be appreciated that some embodiments may perform a number of other post-processing operations on a movement measure. For example, in some embodiments, a movement measure generator may perform operations with saturation (the calculated movement measures are clamped to the boundary values supported by a number of bits used to store those calculated values). In some embodiments, a movement measure generator may cast the calculated movement measure into a 4 bit variable (or 8 bits, 16 bits), which may, in some cases, minimize data volume. In some embodiments, the frequency of occurrences of the calculated movement measures being saturated may be utilized to determine a threshold above which the casting is shifted to generate the movement measures (e.g., to account for "noisier" motion sensors which cause the meaningful data to be in higher order bits of the calculated movement measures). For example, in an embodiment that uses 4 bits to represent the movement measures, a shift of zero means the casting of the movement measures is from bit positions 3:0 of the calculated movement measures, a shift of 1 means the casting of the movement measures is from bit positions 4:1 of the calculated movement measures, and so on.

In some embodiments, a calculated movement measure may include a combination of a statistical measure of the motion data along one or more axes. The statistical measure of the motion data may be one or more of a quantile (e.g., quartile of acceleration data), an inter-quantile range, measures of dispersion (e.g., Gini coefficients), and measures of entropy. In addition, the statistical measures may use information in the frequency domain. The information in the frequency domain may be used to quantify an amount of periodic motion and compare the amount of periodic motion in two or more frequency bands.

Other example techniques of quantifying the distributions of motion data, including accelerometer data, may involve using the standard deviation rather than the maximum minus the minimum, using the interquartile range of motion data, etc.

Other example techniques of quantifying user movements may involve using the temporal derivative (also known as jerk, surge, or lurch) of motion data along each of the three axes, measuring deviations of total acceleration from 1 G (the gravitation acceleration at sea-level on Earth), using integrals of the accelerometer data (e.g., first integral is velocity, second integral is position), etc.

It is noted that acceleration data measured by an accelerometer is provided as an illustrative example of motion data that may be used (alone or in conjunction with sensor data from other sensors of the wearable device 100) to identify swim period(s). Other sensors (e.g., a gyroscope, a gravity sensor, a rotation vector sensor, a magnetometer, etc.) may be used to collect other types of motion data to generate movement measures that may be used (alone or in conjunction with sensor data from other sensors of the wearable device 100) to identify swim period(s).

Boundaries of Swim Periods

Upon identification, one or more identified swim periods may be associated with start times and end times. For example, a given swim period may have a start time of 2:05 PM and end time of 3:15 PM. Alternatively, a swim period may be associated with a start time and a duration (e.g., a start time of 2:05 PM and a duration of 70 minutes).

End of a Swim Period

The device may identify the end of a swim period upon determining that the sensor data is no longer indicative of the user swimming. Alternatively, the device may identify the end of a swim period upon determining that the sensor data no longer most closely corresponds to swimming (e.g., the sensor data more closely corresponds to another user activity).

Relationship Between Swim Metrics and Swim Periods

In one embodiment, identification of swim periods is based on the raw sensor data collected by the wearable device. In another embodiment, identification of swim periods is based on processed data generated by the wearable device. In yet another embodiment, identification of swim periods is based on swim metrics collected by the device. For example, consistent stroke counts and lap counts over a period of time may indicate that the user is more likely to have been swimming during the period of time. In yet another embodiment, identification of swim periods is performed independently of the swim metrics and the swim metrics tracking process.

Multiple Continuous Data Streams

In one embodiment, the swim metrics are collected continuously throughout the day and sent to a central database along with the sensor data (or data based on the sensor data). For example, block 710A of FIG. 7 (described in greater detail below) may correspond to a first data stream and block 710B of FIG. 7 may correspond to a second data stream. Upon sync (e.g., block 715 of FIG. 7), periods of swimming activity are identified, and the swim metrics collected during the identified swim periods are selected and associated with the swim periods based on the timestamp information associated with both of these streams of information (e.g., the collected metrics and the data used for swim period identification).

Processing of Sensor Data

In one embodiment, the wearable device performs all the processing and sends the result (swim metrics and/or swim periods) to the mobile device or the centralized server. In another embodiment, the wearable device determines the swim metrics but the mobile device or server identifies the swim periods based on the sensor data from the wearable device. In yet another embodiment, for one or both of swim metrics tracking and swim period identification, a portion of the processing is performed on the wearable device, and the remaining portion of the processing can be performed on the mobile device or server.

In yet another embodiment, the sensor data is sent to the mobile device or server without any processing. In some of such embodiments, the sensor data is processed by the mobile device or server to determine swim metrics and to identify swim periods.

Example Method for Presenting Swim Metrics

Figure 5:
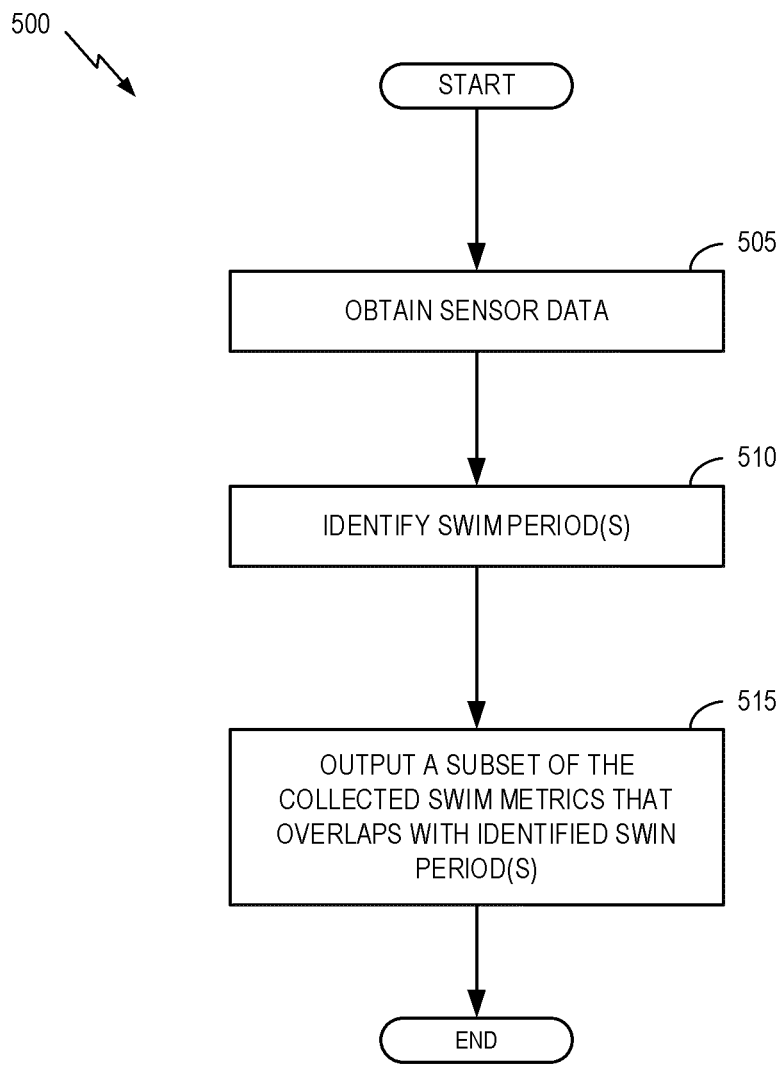
FIG. 5 is a flowchart illustrating an example method for outputting swim metrics in accordance with aspects of this disclosure.

FIG. 5 is a flowchart illustrating an example method for outputting swim metrics in accordance with aspects of this disclosure. The method 500 may be operable by a wearable device 100, or component(s) thereof, for presenting swim metrics or any other activity metrics in accordance with aspects of this disclosure. For example, the steps of method 500 illustrated in FIG. 5 may be performed by a processor 120 of the wearable device 100. In another example, a client device 170 (e.g., a mobile phone) and/or a server 175 in communication with the wearable device 100 may perform at least some of the steps of the method 500. For convenience, the method 500 is described as performed by the wearable device 100.

At block 505, the wearable device 100 obtains sensor data. As described herein, the sensor data may be generated by one or more sensors provided on the wearable device 100. In some embodiments, the wearable device 100 further processes the obtained sensor data. Such processing may include extraction of features relevant to the given activity, such as swimming.

At block 510, the wearable device 100 identifies swim period(s). For example, the wearable device 100 may identify the swim periods using any of the techniques described herein.

At block 515, the wearable device 100 outputs a subset of the collected swim metrics that temporally overlaps with the identified swim periods. For example, if the only identified swim period is from 5 PM to 6 PM on a given day, swim metrics collected during any other time periods (e.g., before 5 PM and after 6 PM) of the given day are ignored and not output (e.g., for presentation to the user).

In the method 500, one or more of the blocks shown in FIG. 5 may be removed (e.g., not performed) and/or the order in which the method is performed may be switched. In some embodiments, additional blocks may be added to the method 500. In addition, as discussed above, although the method 500 is described as being performed by the wearable device 100, another device such as the client device 170 or the server 175 may perform the method 500 instead. The embodiments of the present disclosure are not limited to or by the example shown in FIG. 5, and other variations may be implemented without departing from the spirit of this disclosure.

Example Illustration of Swim Metrics and Swim Periods

Figure 6:
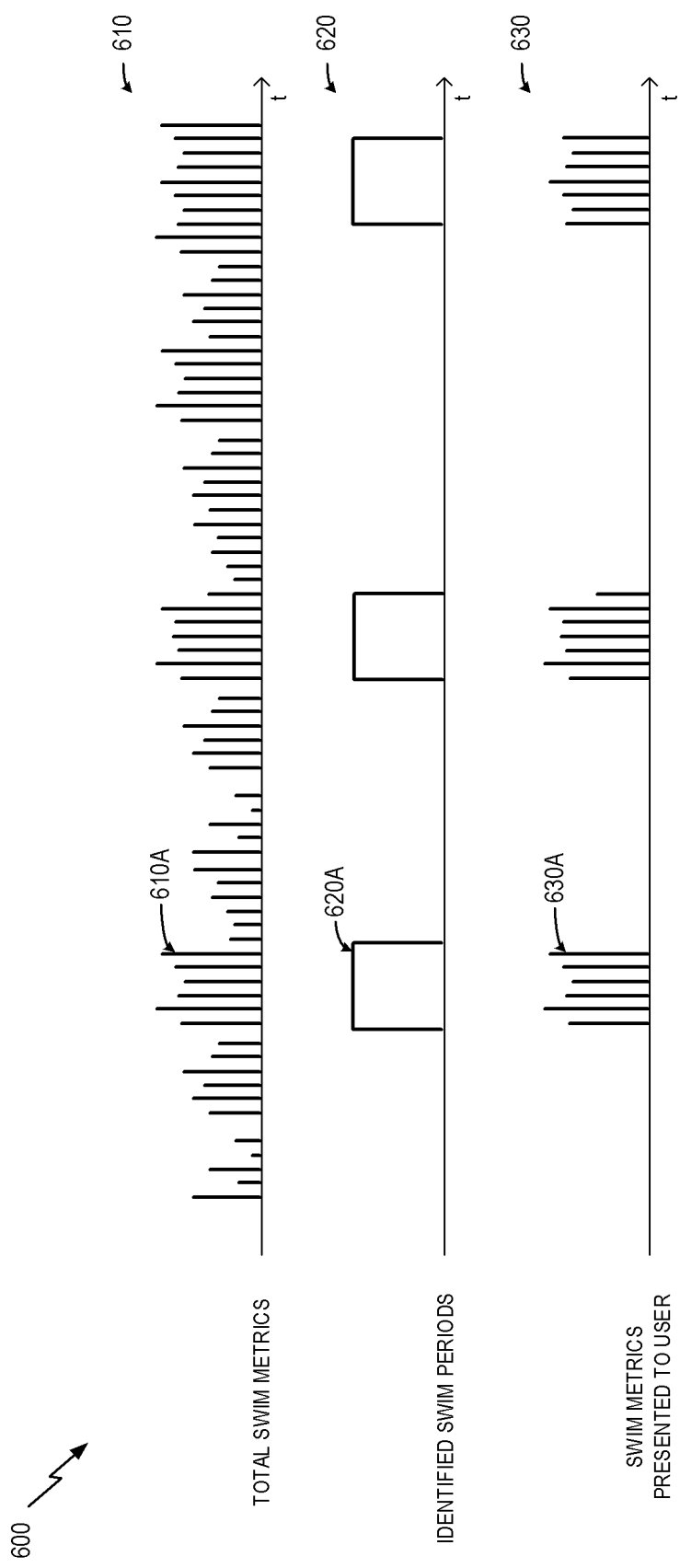
FIG. 6 is a graph illustrating the process of combining the swim metrics and the swim periods in accordance with aspects of this disclosure.

FIG. 6 is a graph 600 illustrating the process of combining the information regarding swim metrics and the swim periods in accordance with aspects of this disclosure. In the example of FIG. 6, the swim metrics are collected throughout the day, and swim periods are identified after the user has finished performing the activity (e.g., swimming). In the example of FIG. 6, each line (e.g., lines 610A and 630A) extending from the horizontal line (labeled t) in top graph 610 and bottom graph 630 represents the number of swim strokes (or the number of laps, kicks, or other metrics, collectively referred to as swim metrics) detected by the wearable device 100 during a unit time period over a period of time (e.g., an extended period, such as, hour(s), throughout the day, etc.). The collected swim metrics are filtered based on the identified swim periods (e.g., to remove swim metrics that do not temporally overlap with one of the identified swim periods) before being presented to the user. As shown in FIG. 6, middle graph 620 shows time periods (e.g., period 620A) during which the user is likely to have been swimming. By collecting swim metrics without receiving any indication (or making any determination) of whether the user is likely to be (or likely to have been) swimming or not, and subsequently filtering the collected swim metrics based on identified swim periods (e.g., periods of time during which the user is like to have been swimming), false positives (e.g., swim stroke counts and other swim metrics collected by the wearable device while the user was not actually swimming) can be eliminated from presentation to the user, thereby enhancing the user experience.

In some embodiments, the mobile application running on the user's mobile device displays a timeline encompassing the earliest swim period of the day through the last swim period of the day. In some of such embodiments, time periods of the day before the earliest swim period of the day and time periods of the day after the last swim period of the day are omitted from the display.

Example Diagram Illustrating Presentation of Swim Metrics

Figure 7:
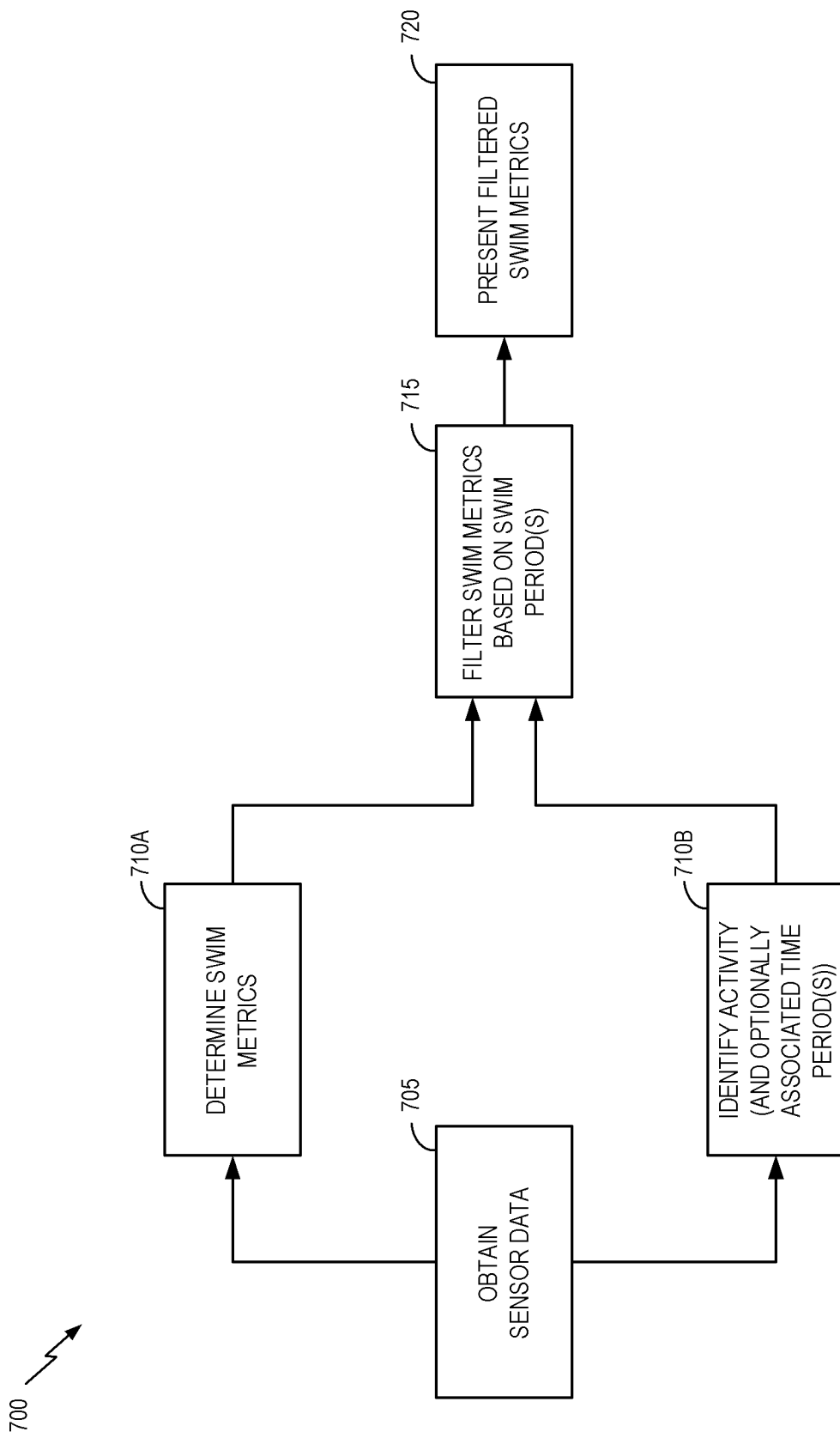
FIG. 7 is a flowchart illustrating an example method for presenting swim metrics in accordance with aspects of this disclosure.

FIG. 7 is a flowchart illustrating an example method for presenting swim metrics in accordance with aspects of this disclosure. The method 700 may be operable by a wearable device 100, or component(s) thereof, for presenting swim metrics or any other activity metrics in accordance with aspects of this disclosure. For example, the steps of method 700 illustrated in FIG. 7 may be performed by a processor 120 of the wearable device 100. In another example, a client device 170 (e.g., a mobile phone) and/or a server 175 in communication with the wearable device 100 may perform at least some of the steps of the method 700. For convenience, the method 700 is described as performed by the wearable device 100.

At block 705, the wearable device 100 generates sensor data. As described herein, the sensor data may be generated by one or more sensors provided on the wearable device 100.

At block 710A, the wearable device 100 determines swim metrics. For example, the determined swim metrics may include lap count, stroke count, stroke type, swim speed, lap duration, etc. As discussed herein, the swim metrics may be determined based on a comparison between samples in the sensor data (e.g., accelerometer, altimeter, and/or other sensor readings) and predefined rules or thresholds corresponding to various types of user movements (e.g., swim stroke, swim kick, turn, etc.). For example, if the sensor data includes a first acceleration peak satisfying a first magnitude condition and a second acceleration peak satisfying a second magnitude condition within a threshold time period from each other, the wearable device 100 may determine that the user has performed a swim stroke. Upon detecting such a swim stroke, the wearable device 100 may increase the swim stroke count by one.

At block 710B, the wearable device 100 identifies the activity being performed by the user. For example, the identified activity may include swimming. In some embodiments, the wearable device 100 may also identify the time periods associated with the identified activity (e.g., periods during which the user is likely to have been performing the identified activity). The identified activity may also include other exercise and/or non-exercise activities. As discussed herein, the activity may be determined based on a comparison between samples in the sensor data (e.g., accelerometer, altimeter, and/or other sensor readings) and predefined rules or thresholds corresponding to various types of user activities (e.g., walking, running, swimming, sleeping, etc.). For example, if the sensor data includes a threshold number of acceleration peaks satisfying a magnitude condition within a threshold time period from each other, the wearable device 100 may determine that the user is swimming. Each user activity may have different rules or thresholds for detection. Block 710B may be performed in real-time, performed after the user has finished performing the identified activity (e.g., post-activity), or performed both in real-time and after the user has finished performing the identified activity.

At block 715, the wearable device 100 filters the swim metrics based on the identified swim periods. For example, the swim metrics may be filtered to remove the swim metrics that do not temporally overlap with one of the identified swim periods (e.g., identified at block 710B). For example, if the wearable device 100 does not (or did not) identify any swim periods at block 710B, the filtered swim metrics would include no swim metrics (e.g., all of the swim metrics determined at block 710A would be removed by the filtering at block 715).

At block 720, the wearable device 100 presents the filtered swim metrics to the user. For example, the filtered swim metrics may be presented to the user via the wearable device 100, a mobile application running on the user's mobile device, and/or an application (e.g., Web browser) running on another computing device.

In the method 700, one or more of the blocks shown in FIG. 7 may be removed (e.g., not performed) and/or the order in which the method is performed may be switched. In some embodiments, additional blocks may be added to the method 700. As discussed above, some of the steps illustrated in FIG. 7 may be performed by a device other than the wearable device 100. For example, the blocks 710B, 715, and 720 may be performed by a mobile device (e.g., client device 170) capable of communicating with the wearable device 100 and/or a server (e.g., server 175) capable of communicating with the wearable device 100 and/or the mobile device. The embodiments of the present disclosure are not limited to or by the example shown in FIG. 7, and other variations may be implemented without departing from the spirit of this disclosure.

Example Method #1 for Performing Real-Time Swim Detection

Figure 8A:
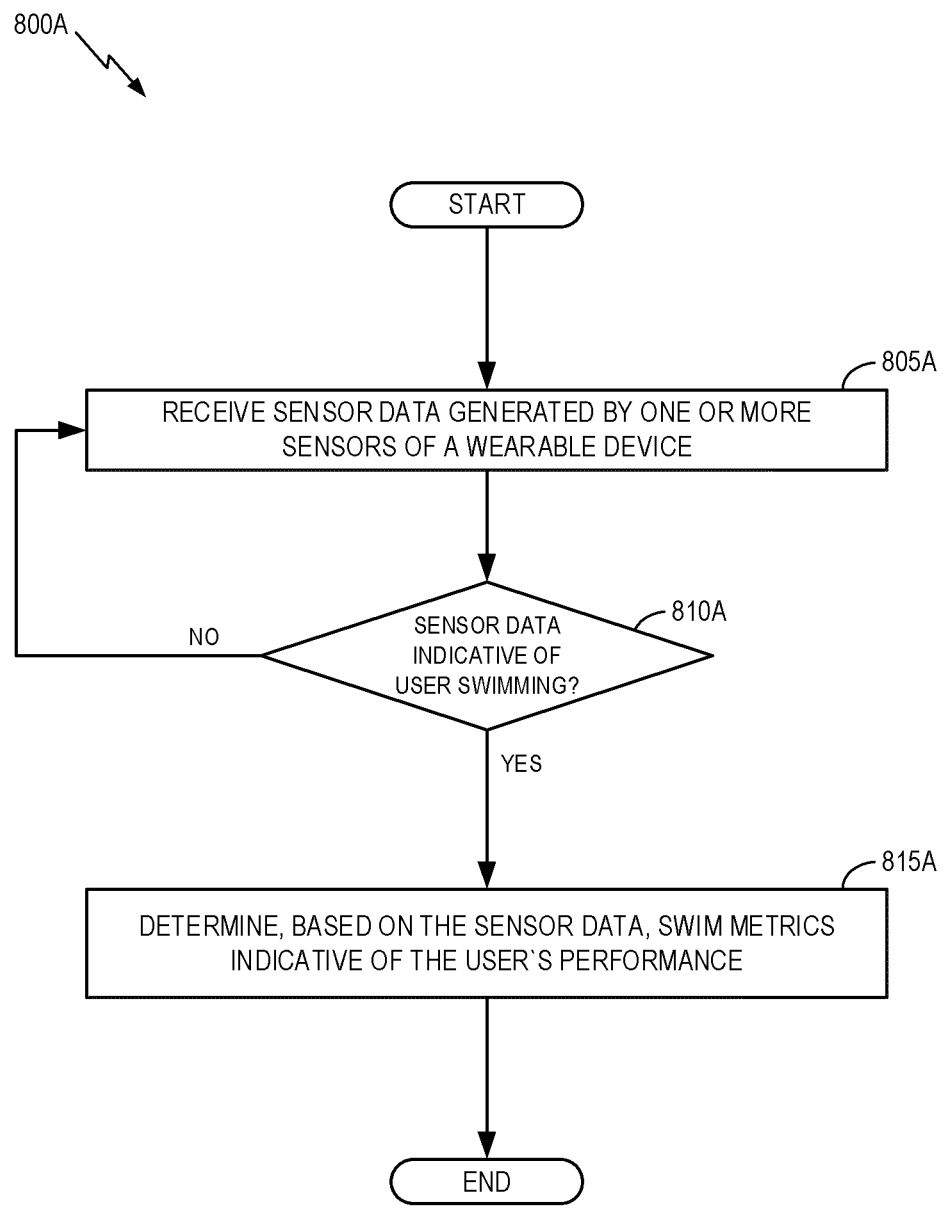
FIG. 8A is a flowchart illustrating an example method for detecting a swimming activity in accordance with aspects of this disclosure.

FIG. 8A is a flowchart illustrating an example method for performing a real-time swim detection in accordance with aspects of this disclosure. The method 800A may be operable by a wearable device 100, or component(s) thereof, for presenting swim metrics or any other activity metrics in accordance with aspects of this disclosure. For example, the steps of method 800A illustrated in FIG. 8A may be performed by a processor 120 of the wearable device 100. In another example, a client device 170 (e.g., a mobile phone) and/or a server 175 in communication with the wearable device 100 may perform at least some of the steps of the method 800A. For convenience, the method 800A is described as performed by the wearable device 100.

At block 805A, the wearable device 100 receives sensor data generated by one or more sensors of the wearable device 100. In some embodiments, the wearable device 100 further processes the received sensor data. Such processing may include extraction of features relevant to the given activity, such as swimming.

At block 810A, the wearable device 100 determines, based on the sensor data, that the user of the wearable device 100 may be swimming. For example, the wearable device 100 may, for each unit time period within a time period for which the sensor data is generated, determine whether the user is more likely to be swimming during the unit time period than performing any other one of a plurality of user activities (e.g., running, hiking, sleeping, etc.) tracked by the wearable device 100. Alternatively, the wearable device 100 may determine, for each unit time period within a time period for which the sensor data is generated, determine whether the sensor data satisfies a threshold condition (e.g., greater than a threshold level of correlation with one or more predefined rules associated with swimming). In response to determining that the user may be swimming, the method 800A proceeds to block 815A. Otherwise, the method 800A returns to block 805A.

At block 815A, the wearable device 100 determines, based on the sensor data, swim metrics indicative of the user's performance with respect to swimming. For example, the wearable device 100 begins collecting or determining swim metrics in response to determining that the user may be swimming. Although not illustrated in FIG. 8A, the method 800A may further include a step in which the wearable device 100 ceases collecting or determining swim metrics in response to determining, based on the sensor data, that the user may no longer be swimming.

In the method 800A, one or more of the blocks shown in FIG. 8A may be removed (e.g., not performed) and/or the order in which the method is performed may be switched. In some embodiments, additional blocks may be added to the method 800A. In addition, as discussed above, although the method 800A is described as being performed by the wearable device 100, another device such as the client device 170 or the server 175 may perform the method 800A instead. The embodiments of the present disclosure are not limited to or by the example shown in FIG. 8A, and other variations may be implemented without departing from the spirit of this disclosure.

Example Method #2 for Performing Real-Time Swim Detection

Figure 8B:
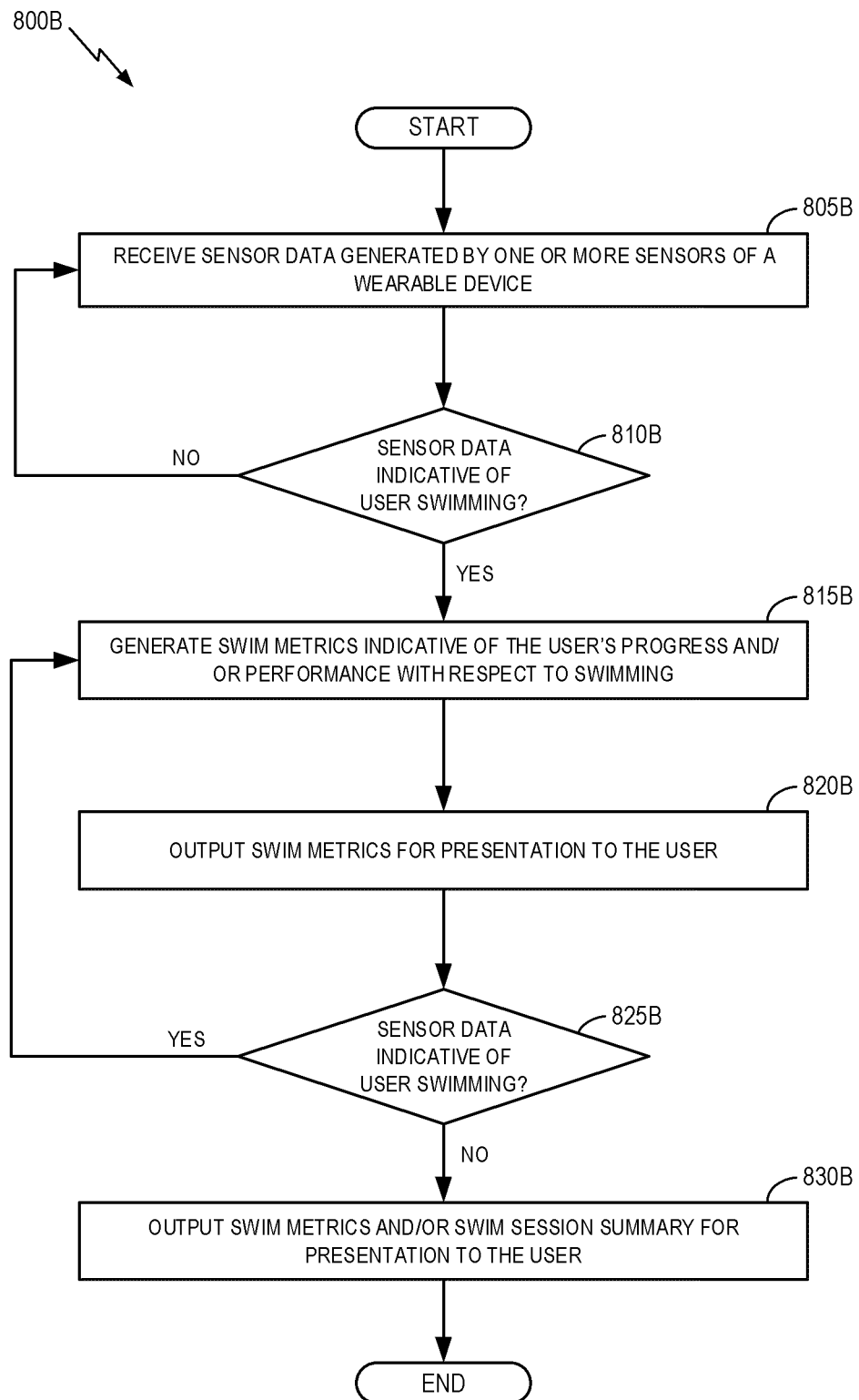
FIG. 8B is a flowchart illustrating an example method for detecting a swimming activity in accordance with aspects of this disclosure.

FIG. 8B is a flowchart illustrating an example method for performing a real-time swim detection in accordance with aspects of this disclosure. The method 800B may be operable by a wearable device 100, or component(s) thereof, for presenting swim metrics or any other activity metrics in accordance with aspects of this disclosure. For example, the steps of method 800B illustrated in FIG. 8B may be performed by a processor 120 of the wearable device 100. In another example, a client device 170 (e.g., a mobile phone) and/or a server 175 in communication with the wearable device 100 may perform at least some of the steps of the method 800B. For convenience, the method 800B is described as performed by the wearable device 100.

At block 805B, the wearable device 100 receives sensor data generated by one or more sensors of the wearable device 100. In some embodiments, the wearable device 100 further processes the received sensor data. Such processing may include extraction of features relevant to the given activity, such as swimming.

At block 810B, the wearable device 100 determines whether the sensor data is indicative of the user swimming. For example, the wearable device 100 may, for each unit time period within a time period for which the sensor data is generated, determine whether the user is more likely to be swimming during the unit time period than performing any other one of a plurality of user activities (e.g., running, hiking, sleeping, etc.) tracked by the wearable device 100. Alternatively, the wearable device 100 may determine, for each unit time period within a time period for which the sensor data is generated, determine whether the sensor data satisfies a threshold condition (e.g., greater than a threshold level of correlation with one or more predefined rules associated with swimming). In some embodiments, the wearable device 100 compares the features extracted from the sensor data to the known features corresponding to swimming (e.g., features indicative of the user swimming). In some embodiments, the wearable device 100 determines that the sensor data is indicative of the user swimming without receiving input indicative of whether the user is swimming. In other embodiments, the wearable device 100 determines that the sensor data is indicative of the user swimming based on input indicating that the user is swimming. In response to determining that the sensor data is indicative of the user swimming, the method 800B proceeds to block 815B. Otherwise, the method 800B returns to block 805B.

At block 815B, the wearable device 100 determines, based on the sensor data, swim metrics indicative of the user's progress and/or performance with respect to swimming. For example, the wearable device 100 begins collecting or determining swim metrics in response to determining the sensor data is indicative of the user swimming.

At block 820B, the wearable device 100 outputs the swim metrics for presentation to the user. For example, the wearable device 100 may display the swim metrics on a display screen of the wearable device 100. Alternatively, the wearable device 100 may wirelessly transmit the swim metrics to the client device 170 wirelessly paired with the wearable device 100 such that the swim metrics can be displayed on a display screen of the client device 170. In another case, the wearable device 100 may wirelessly transmit the swim metrics (e.g., either directly or via the client device 170) to the server 175 for storage and subsequent presentation to the user via the client device 170.

At block 825B, the wearable device 100 determines whether the sensor data is indicative of the user swimming. For example, the wearable device 100 may determine whether the sensor data is indicative of the user swimming in a manner similar to that described above at block 810B. In response to determining that the sensor data is indicative of the user swimming, the method 800B proceeds to block 815B and continues generating the swim metrics. Otherwise, the method 800B proceeds to block 830B, where the wearable device 100 outputs the swim metrics and/or a swim session summary (e.g., a sum or summary of the swim metrics in the current session, such as total swim strokes, total swim laps, total swim duration, average swim speed, average lap time, etc.) for presentation to the user. The wearable device 100 may output the swim metrics and/or the swim session summary in a manner similar to that described above at block 820B.

In the method 800B, one or more of the blocks shown in FIG. 8B may be removed (e.g., not performed) and/or the order in which the method is performed may be switched. In some embodiments, additional blocks may be added to the method 800B. In addition, as discussed above, although the method 800B is described as being performed by the wearable device 100, another device such as the client device 170 or the server 175 may perform the method 800B instead. In some embodiments, one or both of blocks 820B and 830B may be omitted. The embodiments of the present disclosure are not limited to or by the example shown in FIG. 8B, and other variations may be implemented without departing from the spirit of this disclosure.

Adaptive Activation of Sensors

In some embodiments, if device-side swim identification (e.g., swim identification by the wearable device 100) is enabled, upon detecting that the user is swimming (e.g., block 810A of FIG. 8A), the device turns on additional sensors that can be used to calculate more advanced swim metrics such as stroke type or swim speed, but are too expensive in terms of power consumption to keep running continuously. Such sensors include but are not limited to, GPS receivers, altimeters, gyroscopes, magnetometers, and sensor-fusion co-processors. In some embodiments, different types of processing of the sensor data generated by the additional sensors can be enabled. For example, sensor fusion algorithms using accelerometer, gyroscope, and/or magnetometer measurements may be utilized for determining the wearer's orientation and position in space. This additional information (e.g., orientation, position in space, etc.) provides an additional sensory layer upon which advanced swim metrics such as lap count, stroke type, and/or swim period can be more reliably calculated.

Adaptive Mode Switching

In some embodiments, if device-side swim identification (e.g., swim identification by the wearable device 100) is enabled, upon detecting that the user is swimming (e.g., block 810A of FIG. 8A), the device triggers a change in device interaction mode. For example, the swim detection can trigger the loading of an application interface that displays relevant swim metrics. In another example, the swim detection can trigger the toggling to a swim goal mode for devices. In such an example, laps and strokes collected during this period would count toward a pre-set lap/stroke goal for swim sessions, and progress toward this goal can be reflected via a light emitting diode (LED) interface provided on the device. In some embodiments, as long as swimming is detected, the device can display swim metrics via the display screen (e.g., "7 laps in this swim session, time elapsed is 21 minutes").

Different Types of Wearable Devices

The wearable device described herein can be a multi-activity device configured to track activity metrics for a variety of user activities. In another example, the wearable device is a triathlete device configured to track activity metrics for swimming, cycling, and running. As discussed above with reference to FIG. 1C, the wearable device may determine, using the geolocation data, that the wearable device is in or near a body of water (e.g., a swimming pool or an open lake, river, or ocean), and based on such a determination, the wearable device may toggle to a triathlon mode and begin tracking and/or presenting triathlon metrics (e.g., metrics relating to swimming, cycling, and running). In yet another example, the wearable device is a swim-specific device configured to track swim metrics.

Example Method #1 for Performing Post-Activity Swim Detection

Figure 9:
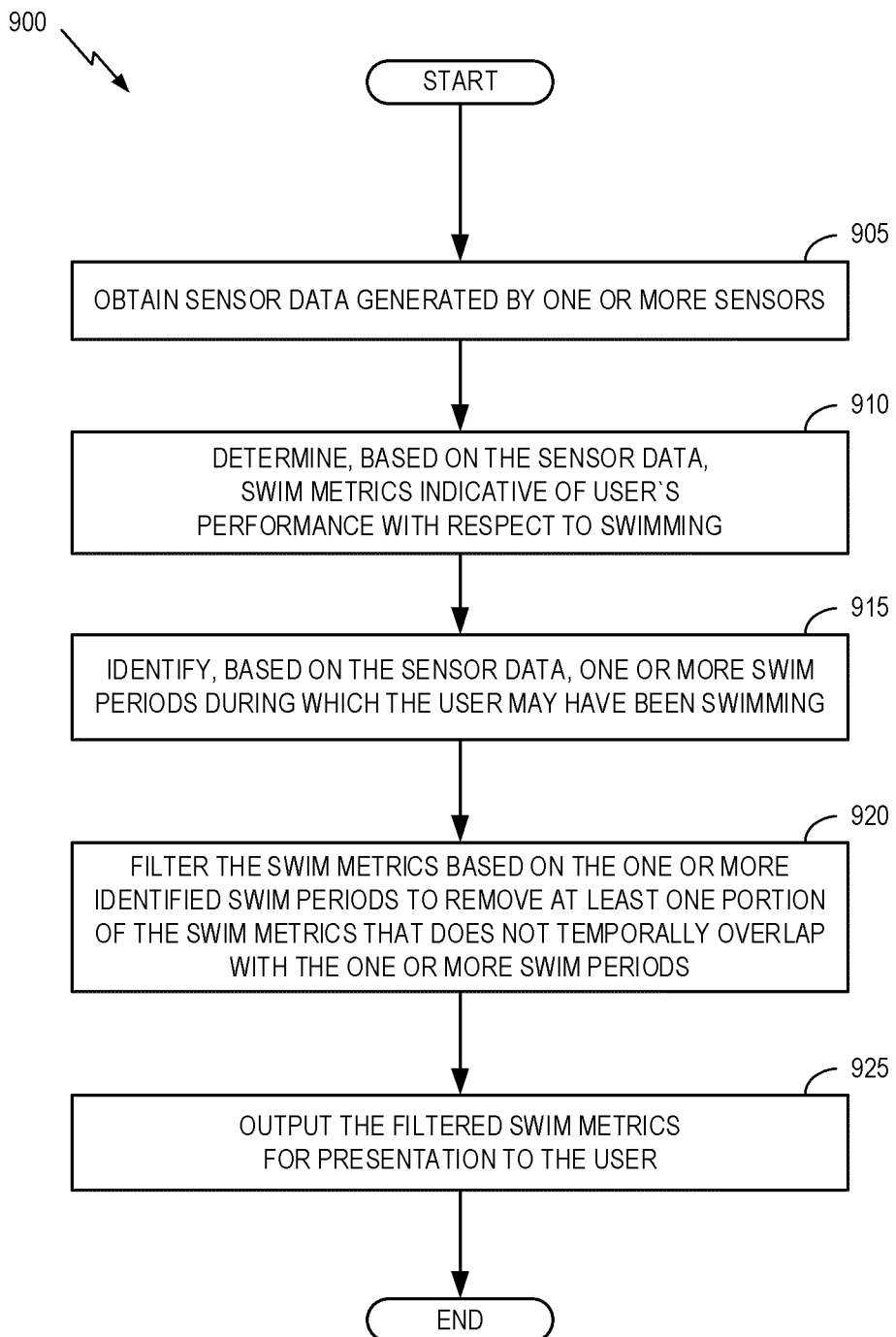
FIG. 9 is a flowchart illustrating an example method for identifying a swim period in accordance with aspects of this disclosure.

FIG. 9 is a flowchart illustrating an example method for performing a real-time swim detection in accordance with aspects of this disclosure. The method 900 may be operable by a wearable device 100, or component(s) thereof, for presenting swim metrics or any other activity metrics in accordance with aspects of this disclosure. For example, the steps of method 900 illustrated in FIG. 9 may be performed by a processor 120 of the wearable device 100. In another example, a client device 170 (e.g., a mobile phone) and/or a server 175 in communication with the wearable device 100 may perform at least some of the steps of the method 900. For convenience, the method 900 is described as performed by the wearable device 100.

At block 905, the wearable device 100 obtains sensor data generated by one or more sensors of the wearable device 100. In some embodiments, the wearable device 100 further processes the obtained sensor data. Such processing may include extraction of features relevant to the given activity, such as swimming.

At block 910, the wearable device 100 determines, based on the sensor data, swim metrics indicative of the user's performance with respect to swimming. In some embodiments, the swim metrics comprise one or more of swim stroke count, swim stroke type, swim kick count, swim lap count, swim lap duration, swim lap start time, swim lap end time, and swim speed. For example, the swim stroke count may be determined based on a number of acceleration peaks extracted from the sensor data that satisfy a set of predefined rules associated with a swim stroke. As another example, the swim lap count may be determined based on a number of breaks between acceleration peaks extracted from the sensor data that span a threshold time period. As another example, the swim lap count may be determined based on a number of acceleration peaks extracted from the sensor data that satisfy a set of predefined rules associated with a flip turn. As another example, the wearable device 100 may include an IMU, and the wearable device 100 may count swim strokes, swim laps, swim kicks, etc. performed by the user based on one or more features extracted from the sensor data generated by the IMU. The IMU may be a 3-axis IMU, a 6-axis IMU, a 9-axis IMU, or any other IMU.

In some embodiments, the wearable device 100 determines the swim metrics in response to determining that the sensor data is indicative of the wearable device 100 being worn (e.g. by the user). For example, the wearable device 100 may determine the sensor data is indicative of the wearable device 100 being worn based on a determination that the sensor data is indicative of movement greater than a threshold level. In such embodiments, the wearable device may, while the swim metrics are being determined, further determine whether the sensor data is no longer indicative of the wearable device being worn, and in response to determining that the sensor data is no longer indicative of the wearable device being worn, cease the determination of the swim metrics.

In some embodiments, the wearable device 100 determines the swim metrics in response to determining that the sensor data is indicative of the user swimming. For example, the wearable device 100 may include an altimeter configured to generate altimeter data indicative of pressure or a pressure change, and the wearable device 100 may determine the swim metrics for one or more time periods for which the altimeter data is indicative of the user swimming (e.g., the pressure change is greater than a threshold level). In another example, the wearable device 100 may include an internal or motion sensor configured to generate user motion data indicative of the user's movement, and the wearable device 100 may determine the swim metrics for one or more time periods for which the user motion data matches a set of predefined motion data associated with swimming.

At block 915, the wearable device 100 identifies, based on the sensor data, one or more swim periods during which the user may have been swimming. For example, the wearable device 100 may, for each unit time period within a time period for which the swim metrics are determined, determine whether swimming is more likely to have been performed during the unit time period than any other one of a plurality of user activities tracked by the wearable device 100, and determine the one or more swim periods based on individual unit time periods for which swimming is determined to be more likely to have been performed than any other one of the plurality of user activities tracked by the wearable device 100. As another example, the wearable device 100 may identify a swim period by determining a start point and an end point of the swim period based on a determination that the sensor data and/or the swim metrics are indicative of the user having (i) started swimming at the start point, (ii) continued to swim until the end point, and (iii) stopped swimming at the end point. The sensor data and/or the swim metrics utilized to identify the swim periods may correspond to a time period that temporally overlaps with, or is subsequent to, the time period during which the sensor data utilized to determine the swim metrics was generated. In some embodiments, the identification of the swim periods occurs subsequent to the determination of the swim metrics. In other embodiments, the identification of the swim periods overlaps at least partially with the period during which the swim metrics are collected or determined.

At block 920, the wearable device 100 filters the swim metrics based on the one or more identified swim periods to remove at least one portion of the swim metrics that does not temporally overlap with the one or more swim periods. For example, the process illustrated in FIG. 6 may be utilized to filter the swim metrics (e.g., select those portions temporally overlapping with the one or more swim periods or remove those portions not temporally overlapping with the one or more swim periods).

At block 925, the wearable device 100 outputs the filtered swim metrics for presentation to the user. For example, the filtered swim metrics may be displayed on a display screen of the wearable device 100.

In the method 900, one or more of the blocks shown in FIG. 9 may be removed (e.g., not performed) and/or the order in which the method is performed may be switched. In some embodiments, additional blocks may be added to the method 900. In addition, as discussed above, although the method 900 is described as being performed by the wearable device 100, another device such as the client device 170 or the server 175 may perform the method 900 instead. The embodiments of the present disclosure are not limited to or by the example shown in FIG. 9, and other variations may be implemented without departing from the spirit of this disclosure.

Example Method #2 for Performing Post-Activity Swim Detection

Figure 10:
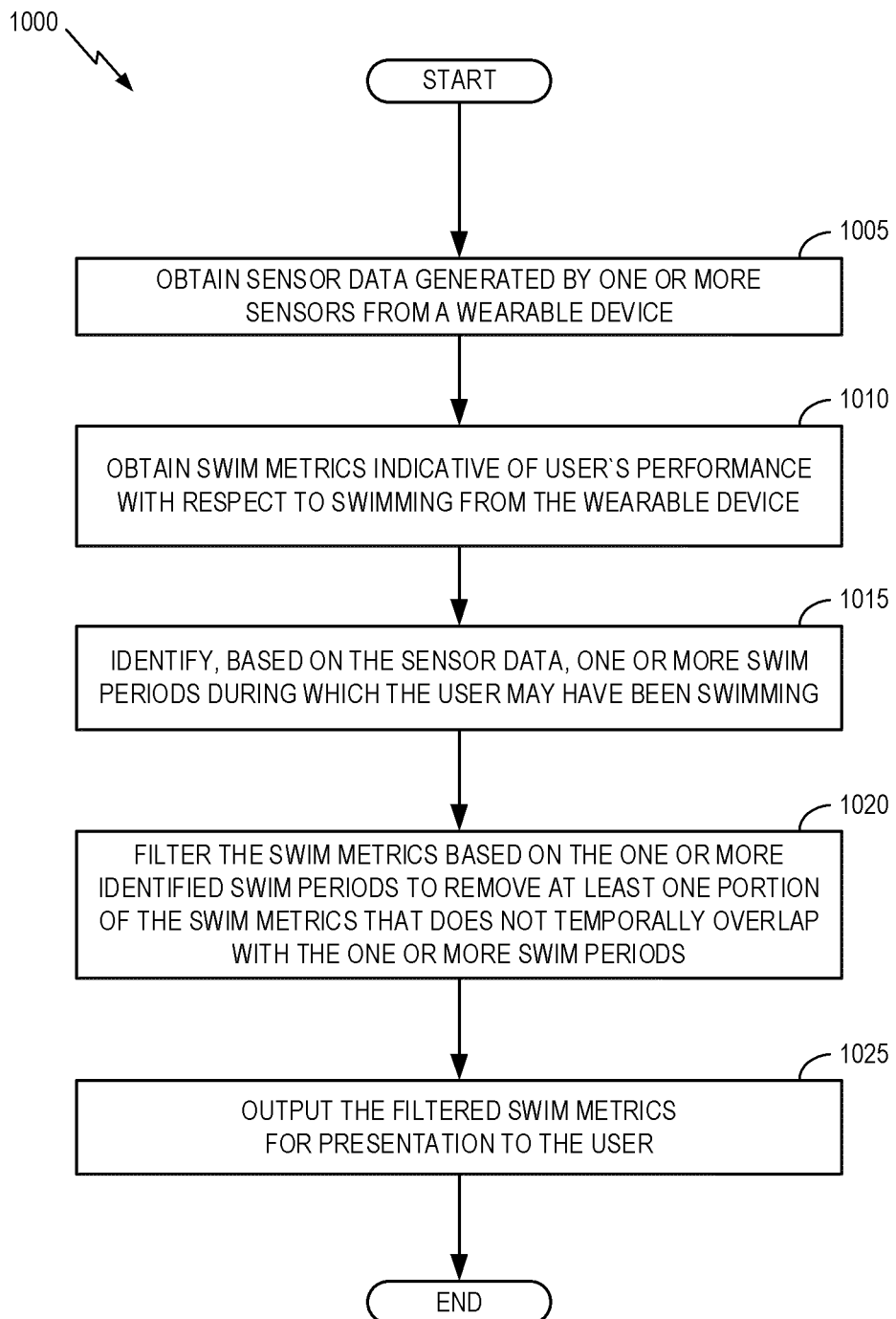
FIG. 10 is a flowchart illustrating an example method for automatic detection and quantification of swimming in accordance with aspects of this disclosure.

FIG. 10 is a flowchart illustrating an example method for performing a real-time swim detection in accordance with aspects of this disclosure. The method 1000 may be operable by a wearable device 100, or component(s) thereof, for presenting swim metrics or any other activity metrics in accordance with aspects of this disclosure. For example, the steps of method 1000 illustrated in FIG. 10 may be performed by a processor 120 of the wearable device 100. In another example, a client device 170 (e.g., a mobile phone) and/or a server 175 in communication with the wearable device 100 may perform at least some of the steps of the method 1000. For convenience, the method 1000 is described as performed by the client device 170.

At block 1005, the client device 170 obtains sensor data generated by one or more sensors of the wearable device 100. In some embodiments, the sensor data is processed by the wearable device 100 before the sensor data is obtained by the client device 170. Alternatively or additionally, the client device 170 may process the sensor data obtained from the wearable device 100. Such processing may include extraction of features relevant to the given activity, such as swimming.

At block 1010, the client device 170 obtains, from the wearable device 100, swim metrics indicative of the user's performance with respect to swimming. Alternatively, the client device 170 may determine the swim metrics based on the sensor data obtained from the wearable device 100. In some embodiments, the swim metrics comprise one or more of swim stroke count, swim stroke type, swim kick count, swim lap count, swim lap duration, swim lap start time, swim lap end time, and swim speed. For example, the swim stroke count may be determined based on a number of acceleration peaks extracted from the sensor data that satisfy a set of predefined rules associated with a swim stroke. As another example, the swim lap count may be determined based on a number of breaks between acceleration peaks extracted from the sensor data that span a threshold time period. As another example, the swim lap count may be determined based on a number of acceleration peaks extracted from the sensor data that satisfy a set of predefined rules associated with a flip turn. As another example, the wearable device 100 may include an IMU, and the wearable device 100 or the client device 170 may count swim strokes, swim laps, swim kicks, etc. performed by the user based on one or more features extracted from the sensor data generated by the IMU. The IMU may be a 3-axis IMU, a 6-axis IMU, a 9-axis IMU, or any other IMU.

At block 1015, the client device 170 identifies, based on the sensor data and/or the swim metrics, one or more swim periods during which the user may have been swimming. For example, the client device 170 may, for each unit time period within a time period for which the swim metrics are determined, determine whether swimming is more likely to have been performed during the unit time period than any other one of a plurality of user activities tracked by the client device 170, and determine the one or more swim periods based on individual unit time periods for which swimming is determined to be more likely to have been performed than any other one of the plurality of user activities tracked by the wearable device 100. As another example, the client device 170 may identify a swim period by determining a start point and an end point of the swim period based on a determination that the sensor data and/or the swim metrics are indicative of the user having (i) started swimming at the start point, (ii) continued to swim until the end point, and (iii) stopped swimming at the end point. The sensor data and/or the swim metrics utilized to identify the swim periods may correspond to a time period that temporally overlaps with, or is subsequent to, the time period during which the sensor data utilized to determine the swim metrics was generated. In some embodiments, the identification of the swim periods occurs subsequent to the determination of the swim metrics. In other embodiments, the identification of the swim periods overlaps at least partially with the period during which the swim metrics are collected or determined.

At block 1020, the client device 170 filters the swim metrics based on the one or more identified swim periods to remove at least one portion of the swim metrics that does not temporally overlap with the one or more swim periods. For example, the process illustrated in FIG. 6 may be utilized to filter the swim metrics (e.g., select those portions temporally overlapping with the one or more swim periods or remove those portions not temporally overlapping with the one or more swim periods).

At block 1025, the client device 170 outputs the filtered swim metrics for presentation to the user. For example, the filtered swim metrics may be displayed on a display screen of the client device 170.

In the method 1000, one or more of the blocks shown in FIG. 10 may be removed (e.g., not performed) and/or the order in which the method is performed may be switched. In some embodiments, additional blocks may be added to the method 1000. In addition, as discussed above, although the method 1000 is described as being performed by the client device 170, another device such as the wearable device 100 or the server 175 may perform the method 1000 instead. The embodiments of the present disclosure are not limited to or by the example shown in FIG. 10, and other variations may be implemented without departing from the spirit of this disclosure.

Example Diagram Illustrating Real-Time and Post-Activity Swim Detections

Figure 11:
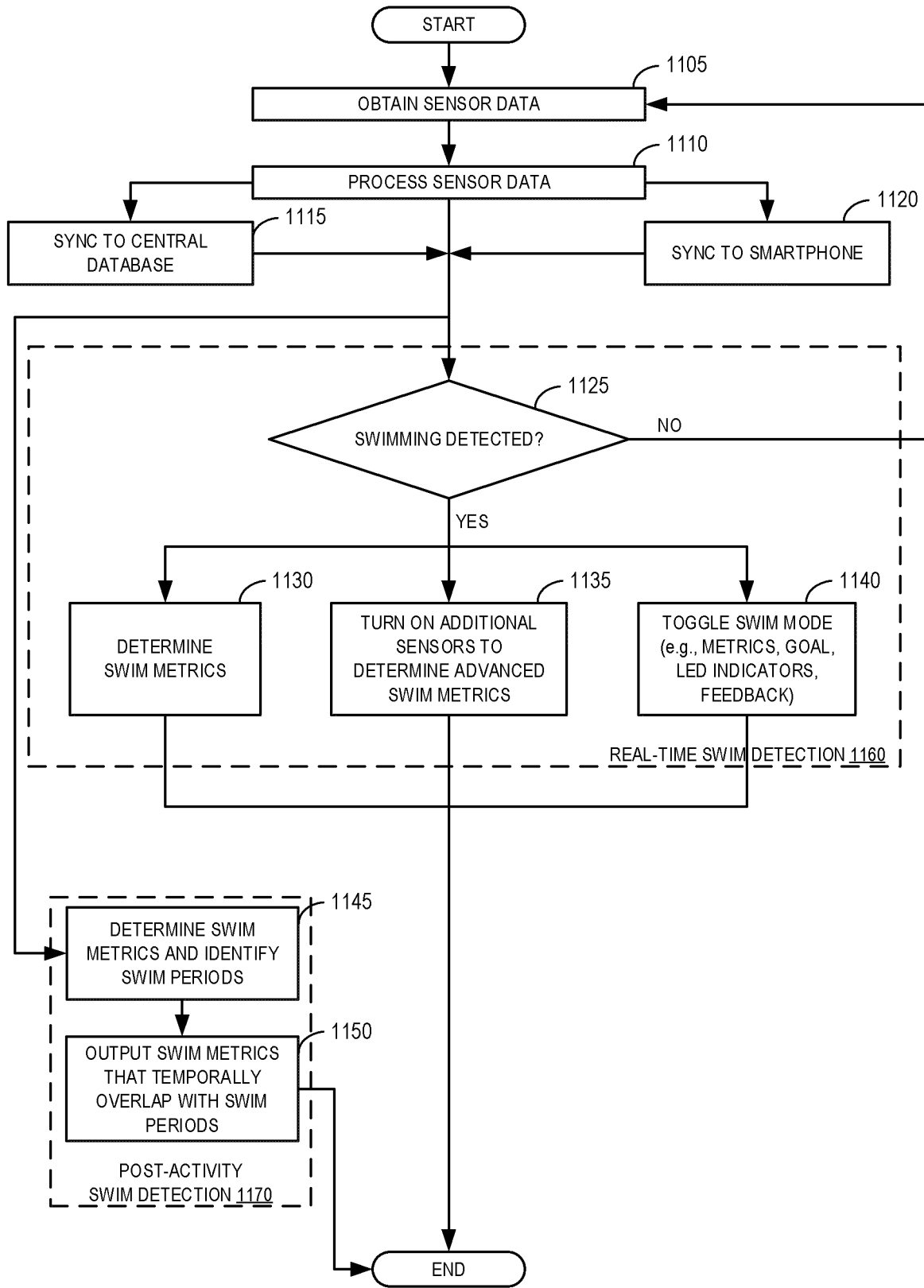
FIG. 11 is a flowchart illustrating an example method for automatic detection and quantification of swimming in accordance with aspects of this disclosure.

FIG. 11 is a flowchart illustrating an example method for presenting swim metrics in accordance with aspects of this disclosure. The method 1100 may be operable by a wearable device 100, a client device 170, a server 175, or any component(s) and/or combination thereof, for detecting and quantifying a user's activity in accordance with aspects of this disclosure. For example, the steps of method 1100 illustrated in FIG. 11 may be performed by a processor 120 of the wearable device 100. In another example, a client device 170 (e.g., a mobile phone) and/or a server 175 in communication with the wearable device 100 may perform at least some of the steps of the method 1100. For convenience, the method 1100 is described as performed by the wearable device 100.

At block 1105, the wearable device 100 obtains sensor data. As described herein, the sensor data may be generated by one or more sensors provided on the wearable device 100. At block 1110, the wearable device 100 processes sensor data. The processing of the sensor data may include extraction of features relevant to the given activity (e.g., features that may be used for identifying the user activity and/or generating activity metrics), such as swimming. The processed sensor data may be utilized for the determinations in blocks 1125, 1130, and/or 1145. Alternatively, raw sensor data generated by the one or more sensors of the wearable device 100 may be utilized for the determinations in blocks 1125, 1130, and/or 1145.

At block 1115, the sensor data or processed sensor data (e.g., data regarding the extracted features) are sent to the central database. The data transmission at block 1115 may occur directly from the wearable device 100 to the central database, or indirectly via another device (e.g., mobile device of the user). At block 1120, the sensor data or processed sensor data are sent to the mobile device of the user (e.g., the user's smartphone).

At decision block 1125, the wearable device 100 determines, based on preliminary sensor data, whether the user is or may be swimming. In response to a determination that the preliminary sensor data does not indicate that the user is or may be swimming, the method 1100 returns to block 1105. Otherwise, the method 1100 proceeds to one or more of blocks 1130, 1135, and 1140.

At block 1130, the wearable device 100 may determine swim metrics. For example, the wearable device 100 may determine swim metrics using any of the techniques described herein.

At block 1135, the wearable device 100 may turn on additional sensors to determine advanced swim metrics. For example, these additional sensors may generate sensor data can be used to identify the swim stroke type and/or swim speed. In some embodiments, these additional sensors include sensors that require a greater amount of power than the accelerometer. In related aspects, one or more additional sensors may be turned on to determine swim-specific metrics, while one or more other sensors that are less relevant or informative with respect to swimming may be turned off or placed into a low-power or standby mode. In further related aspects, block 845 may involve switching from, for example, a 3-axis IMU to a 6-axis IMU or a 9-axis IMU. As noted above, in some embodiments, lower-power sensors such as an accelerometer or altimeter may be used to produce a preliminary or lower-confidence real-time identification of swimming activity, upon which higher-power sensors (e.g., 9-axis IMU sensors) may be briefly toggled on to confirm or improve the confidence in the lower-confidence real-time swim identification.

At block 1140, the wearable device 100 may toggle swim mode(s). In a swim mode, the wearable device 100 may monitor and/or display the user's progress towards a swim goal (e.g., 100 laps per day, 1,000 swim strokes per day, etc.). The user's progress may be indicated the other user interface provided by the wearable device 100 (e.g., via LED lights, visual alerts, information displayed on the display screen, haptic feedback, audible alerts, etc.). In some embodiments, blocks 1125, 1130, 1135, and 1140 may be referred to as real-time swim detection 1160.

Although not illustrated in FIG. 11, in some embodiments, the method 1100 may further include determining whether the sensor data indicates that the user is no longer swimming. In response to a determination that sensor data indicates that the user is no longer swimming, the wearable device 100 may perform one or more of (i) stop determining swim metrics, (ii) turn off the additional sensor(s) activated in response to swim detection (or otherwise place such additional sensor(s) in low power mode), and (iii) deactivate swim mode.

At block 1145, the wearable device 100 may determine swim metrics and identifies swim periods (e.g., based on the sensor data or processed sensor data). In some embodiments, the determination of the swim metrics may occur substantially in real time (e.g., as the user is swimming) and the identification of the swim periods may occur after the user has finished swimming (e.g., upon synchronization of the sensor data and/or the swim metrics with another device). Alternatively, both of the determination of the swim metrics and the identification of the swim periods may occur substantially in real time (e.g., as the user is swimming).

At block 1150, the wearable device 100 may output swim metrics that temporally overlap with the identified swim periods. In some embodiments, blocks 1145 and 1150 may be performed by a device other than the wearable device 100. For example, after the sensor data and/or the swim metrics are synchronized with the user's smartphone at block 1120, the user's smartphone may perform blocks 1145 and 1150. In another example, after the sensor data is synchronized with the central database at block 1115, a server associated with the central database (e.g., server 175) may perform blocks 1145 and 1150 (e.g., output the swim metrics for presentation via a browser on the user's device). The blocks 1145 and 1150 may collectively be referred to as post-activity swim detection 1170.

In the method 1100, one or more of the blocks shown in FIG. 11 may be removed (e.g., not performed) and/or the order in which the method is performed may be switched. For example, in some embodiments, the real-time swim detection 1160 may be omitted. In other embodiments, the post-activity swim detection 1170 may be omitted. In another embodiment, the real-time swim detection 1160 and the post-activity swim detection 1170 may be performed sequentially (e.g., one after the other). In some embodiments, additional blocks may be added to the method 1100. As discussed above, some of the steps illustrated in FIG. 11 may be performed by a device other than the wearable device 100 (e.g., a mobile device such as the client device 170 capable of communicating with the wearable device 100 and/or a server (e.g., the server 175) capable of communicating with the wearable device 100 and/or the mobile device. The embodiments of the present disclosure are not limited to or by the example shown in FIG. 11, and other variations may be implemented without departing from the spirit of this disclosure.

By using a combined approach of collecting the activity metrics all day and automatically identifying the periods during which the activities were actually performed (or most likely to have been performed) by the user, an automatic activity detection and quantification system in which the user is presented with activity metrics without having to interact with the device at all can be provided. It is to be appreciated that embodiments discussed herein may be utilized to realize other advantages.

Example Embodiments

Some embodiments of the disclosure can be described in view of the following clauses:

Clause 1: A method of detecting swimming activity of a user of a wearable device, the wearable device comprising one or more sensors, the method comprising:
  obtaining sensor data generated by the one or more sensors;
  determining, based on the sensor data, swim metrics indicative of the user's performance with respect to swimming;
  identifying, based on the sensor data, one or more swim periods during which the user may have been swimming;
  filtering the swim metrics based on the one or more identified swim periods to remove at least one portion of the swim metrics that does not temporally overlap with the one or more swim periods; and
  outputting the filtered swim metrics for presentation to the user.

Clause 2: The method of clause 1, further comprising:
  determining the swim metrics over a first time period, the determined swim metrics comprising a series of values each corresponding to a unit time period within the first time period; and
  determining, at a second time period subsequent to the first time period, the one or more swim periods within the first time period.

Clause 3: The method of clause 2, further comprising identifying a first swim period starting at a first point in time within the first time period and ending at a second point in time within the first time period based on a determination that the sensor data generated during the first time period is indicative of the user having (i) started swimming at the first point in time, (ii) continued to swim until the second point in time, and (iii) stopped swimming at the second point in time.

Clause 4: The method of clause 2, further comprising identifying a first swim period starting at a first point in time within the first time period and ending at a second point in time within the first time period based on a determination that the sensor data generated during the first time period is indicative of the user having (i) started swimming at the first point in time and (ii) stopped swimming at the second point in time.

Clause 5: The method of clause 1, further comprising:
  for each unit time period within a time period for which the swim metrics are determined, determining whether swimming is more likely to have been performed during the unit time period than any other one of a plurality of user activities tracked by the wearable device; and
  determining the one or more swim periods based on individual unit time periods for which swimming is determined to be more likely to have been performed than any other one of the plurality of user activities tracked by the wearable device.

Clause 6: The method of clause 1, further comprising determining the swim metrics without a determination that the user is or may be swimming or an indication that the user is or may be swimming.

Clause 7: The method of clause 1, further comprising determining the swim metrics in response to a determination that the user is or may be swimming or in response to an indication that the user is or may be swimming.

Clause 8: The method of clause 1, further comprising determining the swim metrics for one or more time periods during which the sensor data is indicative of the wearable device being worn.

Clause 9: The method of clause 8, wherein the sensor data indicative of the wearable device being worn indicates movement greater than a threshold level.

Clause 10: The method of clause 8, further comprising:
- while the swim metrics are being determined, determining whether the sensor data is no longer indicative of the wearable device being worn; and
- in response to determining that the sensor data is no longer indicative of the wearable device being worn, ceasing the determination of the swim metrics.

Clause 11: The method of clause 1, further comprising determining the swim metrics for one or more time periods during which the sensor data is indicative of the user swimming.

Clause 12: The method of clause 11, wherein the sensor data comprises altimeter data indicative of a pressure change, the method further comprising determining that the sensor data is indicative of the user swimming based on the altimeter data.

Clause 13: The method of clause 11, wherein the sensor data comprises user motion data, the method further comprising determining that the sensor data is indicative of the user swimming based on a determination that the user motion data matches a set of predefined motion data associated with swimming.

Clause 14: The method of clause 1, further comprising determining the swim metrics as long as the sensor data is being generated by the one or more sensors.

Clause 15: The method of clause 1, wherein the swim metrics comprise one or more of swim stroke count, swim stroke type, swim kick count, swim lap count, swim lap duration, swim lap start time, swim lap end time, and swim speed.

Clause 16: The method of clause 1, wherein the one or more sensors include an inertial measurement unit, the method further comprising counting swim strokes performed by the user based on one or more features extracted from the sensor data generated by the inertial measurement unit.

Clause 17: The method of clause 1, wherein the one or more sensors include an inertial measurement unit, the method further comprising counting swim laps performed by the user based on one or more features extracted from the sensor data generated by the inertial measurement unit.

Clause 18: The method of clause 1, wherein the wearable device further comprises a geolocation sensor configured to generate geolocation data indicative of a geographic location associated with the swim metrics, the method further comprising determining additional swim metrics based on the geographic location associated with the swim metrics.

Clause 19: The method of clause 1, the method further comprising identifying the one or more swim periods during which the user may have been swimming based on a combination of the sensor data and the swim metrics.

Clause 20: The method of clause 1, further comprising displaying the filtered swim metrics on a display screen of the wearable device.

Clause 21: The method of clause 1, further comprising displaying the filtered swim metrics on a display screen associated with a client device configured to communicate wirelessly with the wearable device.

Clause 22: The method of clause 1, wherein the method is performed by the wearable device.

Clause 23: The method of clause 1, wherein the method is performed by a client device configured to communicate wirelessly with the wearable device.

Clause 24: The method of clause 1, wherein the wearable device further comprises a memory, the method further comprising storing the determined swim metrics in the memory as the swim metrics are determined.

Clause 25: A method of detecting swimming activity of a user of a wearable device, the wearable device comprising one or more sensors, the method comprising:
- obtaining sensor data generated by the one or more sensors from the wearable device;
- obtaining swim metrics indicative of the user's performance with respect to swimming from the wearable device;
- identifying, based on the sensor data, one or more swim periods during which the user may have been swimming;
- filtering the swim metrics based on the one or more identified swim periods to remove at least one portion of the swim metrics that does not temporally overlap with the one or more swim periods; and
- outputting the filtered swim metrics for presentation to the user.

Clause 26: The method of clause 25, wherein the method is performed by a client device configured to communicate with the wearable device, the method further comprising displaying the filtered swim metrics on a display screen of the client device.

Clause 27: The method of clause 25, wherein the swim metrics are determined over a first time period, the determined swim metrics comprising a series of values each corresponding to a unit time period within the first time period, the method further comprising determining, at a second time period subsequent to the first time period, the one or more swim periods within the first time period.

Clause 28: The method of clause 27, further comprising identifying a first swim period starting at a first point in time within the first time period and ending at a second point in time within the first time period based on a determination that the sensor data generated during the first time period is indicative of the user having (i) started swimming at the first point in time, (ii) continued to swim until the second point in time, and (iii) stopped swimming at the second point in time.

Clause 29: The method of clause 27, further comprising identifying a first swim period starting at a first point in time within the first time period and ending at a second point in time within the first time period based on a determination that the sensor data generated during the first time period is indicative of the user having (i) started swimming at the first point in time and (ii) stopped swimming at the second point in time.

Clause 30: The method of clause 25, further comprising:
- for each unit time period within a time period for which the swim metrics are determined, determining whether swimming is more likely to have been performed during the unit time period than any other one of a plurality of user activities tracked by the wearable device; and
- determining the one or more swim periods based on individual unit time periods for which swimming is determined to be more likely to have been performed than any other one of the plurality of user activities tracked by the wearable device.

Clause 31: The method of clause 25, wherein the swim metrics are determined without a determination that the user is or may be swimming or an indication that the user is or may be swimming.

Clause 32: The method of clause 25, wherein the swim metrics are determined in response to a determination that the user is or may be swimming or in response to an indication that the user is or may be swimming.

Clause 33: The method of clause 25, wherein the swim metrics are determine for one or more time periods during which the sensor data is indicative of the wearable device being worn.

Clause 34: The method of clause 33, wherein the sensor data indicative of the wearable device being worn indicates movement greater than a threshold level.

Clause 35: The method of clause 33, further comprising:
while the swim metrics are being determined, determining whether the sensor data is no longer indicative of the wearable device being worn; and
in response to determining that the sensor data is no longer indicative of the wearable device being worn, ceasing the determination of the swim metrics.

Clause 36: The method of clause 33, wherein the swim metrics are determined for one or more time periods during which the sensor data is indicative of the user swimming.

Clause 37: The method of clause 36, wherein the sensor data comprises altimeter data indicative of a pressure change, and the swim metrics are determined for the one or more time periods for which the altimeter data is indicative of the user swimming.

Clause 38: The method of clause 36, wherein the sensor data comprises user motion data, and the swim metrics are determined for the one or more time periods for which the user motion data matches a set of predefined motion data associated with swimming.

Clause 39: The method of clause 25, wherein the swim metrics comprise one or more of swim stroke count, swim stroke type, swim kick count, swim lap count, swim lap duration, swim lap start time, swim lap end time, and swim speed.

Clause 40: The method of clause 25, wherein the sensor data further comprises geolocation data indicative of a geographic location associated with the swim metrics, the method further comprising determining additional swim metrics based on the geographic location associated with the swim metrics.

Clause 41: The method of clause 25, further comprising identifying the one or more swim periods during which the user may have been swimming based on a combination of the sensor data and the swim metrics.

Clause 42: The method of clause 25, further comprising periodically obtaining the sensor data and the swim metrics from the wearable device.

Clause 43: The method of clause 25, further comprising obtaining the sensor data and the swim metrics from the wearable device upon establishing of a wireless connection with the wearable device.

Clause 44: A method of detecting swimming activity of a user of a wearable device, the wearable device comprising one or more sensors, the method comprising:
receiving sensor data generated by the one or more sensors;
determining, based on the sensor data, that the user may be swimming; and
determining, based on the sensor data, swim metrics indicative of the user's performance in response to determining that the user may be swimming.

Clause 45: The method of clause 44, further comprising activating one or more additional sensors for generating additional sensor data in response to determining that the user may be swimming.

Clause 46: The method of clause 44, further comprising activating a swim mode to monitor the user's progress or performance with respect to swimming in response to determining that the user may be swimming.

Clause 47: The method of clause 44, further comprising:
while determining the swim metrics, determining, based on the sensor data, that the user may no longer be swimming; and
in response to determining that the user may no longer be swimming, ceasing the determination of the swim metrics.

Clause 48: The method of clause 44, further comprising determining whether the user may be swimming without receiving an input from the user indicative of whether the user is swimming.

Clause 49: The method of clause 44, further comprising determining whether the user may be swimming based on a user input indicative of whether the user is swimming.

Clause 50: The method of clause 44, further comprising:
determining whether the user may be swimming based on sensor data generated during a first time period; and
generating the swim metrics based on sensor data generated during a second time period that is subsequent to the first time period.

Clause 51: The method of clause 44, further comprising:
determining whether the user may be swimming based on sensor data generated during a first time period; and
generating the swim metrics based on a combination of the sensor data generated during the first time period and sensor data generated during a second time period that is subsequent to the first time period.

Clause 52: The method of clause 44, further comprising:
for each unit time period within a time period for which the sensor data is generated, determining whether the user is more likely to be swimming during the unit time period than performing any other one of a plurality of user activities tracked by the wearable device; and
generating the swim metrics during one or more individual unit time periods for which the user is determined to be more likely to be swimming than performing any other one of the plurality of user activities tracked by the wearable device.

Clause 53: The method of clause 44, wherein the swim metrics comprise one or more of swim stroke count, swim stroke type, swim kick count, swim lap count, swim lap duration, swim lap start time, swim lap end time, and swim speed.

Clause 54: The method of clause 44, wherein the one or more sensors include an inertial measurement unit, the method further comprising counting swim strokes performed by the user based on one or more features extracted from the sensor data generated by the inertial measurement unit.

Clause 55: The method of clause 44, wherein the one or more sensors include an inertial measurement unit, the method further comprising counting swim laps performed by the user based on one or more features extracted from the sensor data generated by the inertial measurement unit.

Clause 56: The method of clause 44, wherein the wearable device further comprises a geolocation sensor configured to generate geolocation data indicative of a geographic location associated with the swim metrics, the method further comprising determining additional swim metrics based on the geographic location associated with the swim metrics.

Clause 57: The method of clause 44, wherein the method is performed by the wearable device, the method further comprising displaying, on a display screen of the wearable device, a message that comprises at least one of text and graphics indicative of the user's performance with respect to swimming.

Clause 58: The method of clause 44, wherein the method is performed by a client device that is wirelessly paired with the wearable device, the method further comprising transmitting instructions to wearable device to display a message that comprises at least one of text and graphics indicative of the user's performance with respect to swimming.

Clause 59: The method of clause 44, wherein the method is performed by a client device that is wirelessly paired with the wearable device, the method further comprising displaying, on a display screen associated with the client device, a message that comprises at least one of text and graphics indicative of the user's performance with respect to swimming.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, FPGAs, or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

What is claimed is:

1. A system comprising:
one or more memories; and
one or more processors, wherein:
 the one or more processors and the one or more memories are operably connected, and
 the one or more memories store computer-executable instructions which, when executed by the one or more processors, cause the one or more processors to:
  obtain sensor data generated by one or more sensors of either a) a wearable device associated with a user or b) the wearable device and a client device also associated with the user,
  determine, based on the sensor data indicating that one or more predetermined conditions are met that are indicative of an increased likelihood that the user is swimming, that collection of swim metrics indicative of a user's performance with respect to swimming should begin,
  collect, responsive to determining that the collection of the swim metrics should begin and without any user input provided via a user interface, the swim metrics during a first time period based on the sensor data, identify, based on the sensor data and without any user input provided via the user interface, one or more swim periods in the first time period in which the user was swimming for at least a portion thereof, filter the swim metrics based on the one or more identified swim periods, and cause at least some of the filtered swim metrics to be output for presentation to the user such that any portion of the swim metrics that does not temporally overlap with any of the one or more swim periods is not caused to be output for presentation to the user.

2. The system of claim 1, wherein the memory further stores additional computer-executable instructions which, when executed by the one or more processors, further cause the one or more processors to identify the one or more swim periods at a time after the first time period, wherein the collected swim metrics comprise a series of values that each correspond to a unit time period of a plurality of unit time periods within the first time period.

3. The system of claim 1, wherein the memory further stores additional computer-executable instructions which, when executed by the one or more processors, further cause the one or more processors to identify a first swim period starting at a first point in time within the first time period and ending at a second point in time within the first time period based on determining that the sensor data generated during the first time period is indicative of the user having (i) started swimming at the first point in time, (ii) continued to swim until the second point in time, and (iii) stopped swimming at the second point in time.

4. The system of claim 1, wherein the memory further stores additional computer-executable instructions which, when executed by the one or more processors, further cause the one or more processors to:
- determine, for each respective unit time period of a plurality of unit time periods within the first time period for which the swim metrics are collected, whether swimming is more likely to have been performed during the respective unit time period than any other one of a plurality of user activities tracked by the wearable device; and
- identify the one or more swim periods based on the unit time periods for which swimming is determined to be more likely to have been performed than any other one of the plurality of user activities tracked by the wearable device.

5. A method of tracking swim metrics for a user associated with a wearable device, the method comprising:
- obtaining, by one or more processors, sensor data generated by one or more sensors of either a) the wearable device or b) the wearable device and a client device also associated with the user;
- determining, by the one or more processors and based on the sensor data indicating that one or more predetermined conditions are met that are indicative of an increased likelihood that the user is swimming, that collection of swim metrics indicative of the user's performance with respect to swimming should begin;
- collecting, by the one or more processors, responsive to determining that the collection of the swim metrics should begin, and without any user input provided via a user interface, the swim metrics during a first time period based on the sensor data;
- identifying, by the one or more processors, based on the sensor data, and without any user input provided via the user interface, one or more swim periods in the first time period in which the sensor data indicates that the user was swimming for at least a portion thereof;
- filtering, by the one or more processors, the swim metrics based on the one or more identified swim periods; and
- causing, by the one or more processors, the filtered swim metrics to be output to the user such that any portion of the swim metrics that does not temporally overlap with any of the one or more swim periods is not output for presentation to the user.

6. The method of claim 5, wherein:
the collected swim metrics comprise a series of values that each correspond to a unit time period of a plurality of unit time periods within the first time period, and
the identification of the one or more swim periods within the first time period occurs at a time after the first time period.

7. The method of claim 6, further comprising identifying, by the one or more processors, a first swim period starting at a first point in time within the first time period and ending at a second point in time within the first time period based on determining that the sensor data generated during the first time period is indicative of the user having (i) started swimming at the first point in time, (ii) continued to swim until the second point in time, and (iii) stopped swimming at the second point in time.

8. The method of claim 5, further comprising:
- determining, for each respective unit time period of a plurality of unit time periods within the first time period for which the swim metrics are collected, whether swimming is more likely to have been performed during the respective unit time period than any other one of a plurality of user activities tracked by the wearable device; and
- identifying the one or more swim periods based on the unit time periods for which swimming is determined to be more likely to have been performed than any other one of the plurality of user activities tracked by the wearable device.

9. The method of claim 5, further comprising activating one or more additional sensors of the wearable device in order to collect the swim metrics during the first time period.

10. The method of claim 5, wherein the one or more predetermined conditions include a condition that is met when the sensor data indicates user movement greater than a threshold level.

11. The method of claim 10, further comprising:
- determining, by the one or more processors and while the swim metrics are being collected, that the sensor data indicates user movement less than the threshold level; and
- ceasing, in response to determining that the sensor data indicates user movement less than the threshold level, the collection of the swim metrics.

12. The method of claim 5, wherein the sensor data comprises altimeter data indicative of a pressure change and the method further comprises identifying, by the one or more processors, the one or more swim periods based on the altimeter data.

13. The method of claim 5, wherein the sensor data comprises user motion data and the method further comprises identifying, by the one or more processors, the one or more swim periods based on determining that the user motion data matches a set of predefined motion data associated with swimming.

14. The method of claim 5, wherein the wearable device further comprises or is communicatively connected with another device that has, a geolocation sensor configured to generate geolocation data indicative of a geographic location associated with swimming and the method further comprises determining additional swim metrics based on the geographic location associated with swimming.

15. Non-transitory physical computer storage storing computer-executable instructions that, when executed by one or more processors, cause the one or more processors to:
 obtain sensor data generated by one or more sensors of either a) a wearable device associated with a user or b) the wearable device and a client device also associated with the user,
 determine, based on the sensor data indicating that one or more predetermined conditions are met that are indicative of an increased likelihood that the user is swimming, that collection of swim metrics indicative of a user's performance with respect to swimming should begin,
 collect, responsive to determining that the collection of the swim metrics should begin and without any user input provided via a user interface, the swim metrics during a first time period based on the sensor data,
 identify, based on the sensor data and without any user input provided via the user interface, one or more swim periods in the first time period in which the user was swimming for at least a portion thereof,
 filter the swim metrics based on the one or more identified swim periods, and
 cause at least some of the filtered swim metrics to be output for presentation to the user such that any portion of the swim metrics that does not temporally overlap with any of the one or more swim periods is not caused to be output for presentation to the user.

16. The non-transitory physical computer storage of claim 15, further storing additional computer-executable instructions that, when executed by the one or more processors, further cause the one or more processors to identify the one or more swim periods at a time after the first time period, wherein the collected swim metrics comprise a series of values that each correspond to a unit time period of a plurality of unit time periods within the first time period.

17. The non-transitory physical computer storage of claim 15, further storing additional computer-executable instructions that, when executed by the one or more processors, further cause the one or more processors to identify a first swim period starting at a first point in time within the first time period and ending at a second point in time within the first time period based on determining that the sensor data generated during the first time period is indicative of the user having (i) started swimming at the first point in time, (ii) continued to swim until the second point in time, and (iii) stopped swimming at the second point in time.

18. The non-transitory physical computer storage of claim 15, further storing additional computer-executable instructions that, when executed by the one or more processors, further cause the one or more processors to:
 determine, for each respective unit time period of a plurality of unit time periods within the first time period for which the swim metrics are collected, whether swimming is more likely to have been performed during the respective unit time period than any other one of a plurality of user activities tracked by the wearable device; and
 identify the one or more swim periods based on the unit time periods for which swimming is determined to be more likely to have been performed than any other one of the plurality of user activities tracked by the wearable device.

19. The non-transitory physical computer storage of claim 15, wherein the non-transitory physical computer storage further stores additional computer-executable instructions that, when executed by the one or more processors, further cause the one or more processors to cause one or more additional sensors of the wearable device to be activated in order to collect the swim metrics during the first time period.

20. The non-transitory physical computer storage of claim 15, wherein the non-transitory physical computer storage further stores additional computer-executable instructions that, when executed by the one or more processors, further cause the one or more processors to:
 determine that the collection of the swim metrics for the first time period should begin based on the sensor data indicating user movement greater than a threshold level,
 determine, while the swim metrics are being collected, that the sensor data indicates that the user movement is less than the threshold level; and
 cease, in response to determining that the sensor data indicates that the user movement is less than the threshold level, the collection of the swim metrics for the first time period.

* * * * *